United States Patent [19]

Terada et al.

[11] Patent Number: 5,698,576
[45] Date of Patent: Dec. 16, 1997

[54] USE OF IMIDAZOPYRAZOLE DERIVATIVES AS ANALGESICS ANTI-INFLAMMATORY AGENTS

[75] Inventors: Atsusuke Terada; Kazuyuki Wachi; Hachio Miyazawa; Yoshio Iizuka; Kazuo Hasegawa; Keiichi Tabata, all of Tokyo, Japan

[73] Assignee: Sankyo Company, Limited, Tokyo, Japan

[21] Appl. No.: 755,290

[22] Filed: Nov. 22, 1996

Related U.S. Application Data

[62] Division of Ser. No. 418,825, Apr. 7, 1995, which is a division of Ser. No. 260,896, Jun. 16, 1994, which is a division of Ser. No. 975,987, Nov. 13, 1992, Pat. No. 5,354,768, which is a continuation of Ser. No. 831,004, Feb. 6, 1992, abandoned, which is a continuation of Ser. No. 620,839, Nov. 29, 1990, abandoned, which is a division of Ser. No. 596,578, Oct. 10, 1990, abandoned, which is a continuation of Ser. No. 384,725, Jul. 25, 1989, abandoned.

[30] Foreign Application Priority Data

Jul. 26, 1988 [JP] Japan ................................. 6-186132

[51] Int. Cl.⁶ ...................... A61K 31/415; C07D 235/00
[52] U.S. Cl. ............. 514/393; 548/303.1; 514/228.5; 514/232.8; 514/255; 514/269; 514/307; 514/314; 514/322; 514/338; 514/365; 514/372; 514/374; 514/378; 514/383
[58] Field of Search .................... 514/393; 548/303.1

[56] References Cited

U.S. PATENT DOCUMENTS

| | | | |
|---|---|---|---|
| 4,500,630 | 2/1985 | Sato et al. | 430/372 |
| 4,585,771 | 4/1986 | Klose et al. | 514/393 |
| 4,639,415 | 1/1987 | Kaneko et al. | 548/324 |
| 4,719,218 | 1/1988 | Bender et al. | 514/393 |
| 4,752,561 | 6/1988 | Nishijima et al. | 548/324 |
| 4,788,134 | 11/1988 | Ozaki et al. | 430/353 |
| 5,232,939 | 8/1993 | Terada et al. | 514/393 |

FOREIGN PATENT DOCUMENTS

| | | |
|---|---|---|
| 62-96940 | 5/1987 | Japan . |
| WO 86/02467 | 4/1986 | WIPO . |

OTHER PUBLICATIONS

Chemical Abstracts, vol. 82, No. 6 Abstracts 42, 451w, Feb. 10, 1973, p. 363.
Chemical Abstracts, vol. 82, No. 22, Abstract 156174p, Jun. 2, 1975, p. 597.
Kline, Ira, CA 81:45352, 1974.

*Primary Examiner*—Johann Richter
*Assistant Examiner*—Laura L. Stockton
*Attorney, Agent, or Firm*—Frishauf, Holtz, Goodman, Langer & Chick, P.C.

[57] ABSTRACT

Described herein are compounds of formula (I):

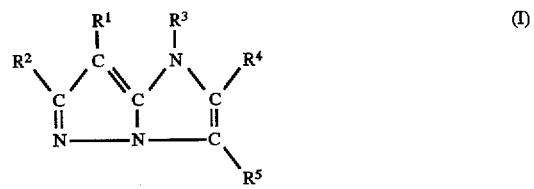

[in which: $R^1$ and $R^2$ are hydrogen, optionally substituted alkyl, cycloalkyl, alkenyl, aralkyl, arylalkenyl, aryl, aromatic heterocyclic, cyano or halogen; $R^3$ is hydrogen, optionally substituted alkyl, aralkyl or acyl; $R^4$ and $R^5$ are hydrogen, optionally substituted alkyl, cycloalkyl, alkenyl, aralkyl, arylalkenyl, aryl or aromatic heterocyclic]; and pharmaceutically acceptable salts thereof are analgesics and anti-inflammatory agents as well having anti-ulcer and 5-lipoxygenase inhibitory activities.

12 Claims, No Drawings

USE OF IMIDAZOPYRAZOLE DERIVATIVES AS ANALGESICS ANTI-INFLAMMATORY AGENTS

This is a division of application Ser. No. 08/418,825 filed Apr. 7, 1995, which is a divisional of application Ser. No. 08/260,896, filed Jun. 16, 1994, which is a division of Ser. No. 07/975,987 filed Nov. 13, 1992, (now U.S. Pat. No. 5,354,768), which is a continuation of Ser. No. 07/831,004 filed Feb. 6, 1992 (abandoned) which is a continuation of Ser. No. 07/620,839 filed Nov. 29, 1990 (abandoned), which is a divisional of Ser. No. 07/596,578 filed Oct. 10, 1990 (abandoned), which is a continuation of Ser. No. 07/384,725 filed Jul. 25, 1989 (abandoned).

BACKGROUND TO THE INVENTION

The present invention relates to the use of a class of imidazopyrazole derivatives as analgesics and anti-inflammatory agents as well as for a number of other unexpected and valuable therapeutic purposes, specifically anti-ulcer and 5-lipoxygenase inhibitory activities. The invention also provides as new compositions of matter certain novel compounds falling within this class and provides processes for preparing these compounds.

The compounds of the present invention have a variety of therapeutic activities, including an analgesic and anti-inflammatory effect. A number of compounds having this type of activity is known, aspirin being, perhaps, the best known of these. However, like aspirin, the known compounds having this type of activity have one major disadvantage: they tend to cause problems in the digestive tract, and may ultimately cause ulcers. Most surprisingly, we have found that the compounds of the present invention, far from causing ulcers, actually have an anti-ulcer activity to an extent that they may have value as anti-ulcer agents in their own right.

Certain of the compounds employed in the present invention are known from U.S. Pat. No. 4,500,630 and No. 4,788,134 and from J. Heterocyclic Chem., 411–413 (1973). There is no utility disclosed in the J. Heterocyclic Chem. article, and the U.S. patents only disclose the compounds as couplers for photographic materials and as silver salts for use in photographic materials, respectively. There is absolutely no suggestion in any of the prior art of which we are aware that the compounds employed in the present invention have any therapeutic activity still less that they have the excellent and valuable range of activities that we have unexpectedly found, and, so far as we are aware, compounds of this type have never previously been proposed for therapeutic use.

BRIEF SUMMARY OF INVENTION

In particular, we have found that the compounds of the present invention have the following activities: analgesic and anti-inflammatory; anti-ulcer; and 5-lipoxygenase inhibitory activity.

It is an object of the present invention to provide a series of compounds having analgesic and anti-inflammatory activities.

It is a further object of the invention to provide compounds having anti-ulcer activity.

It is a still further object of the invention to provide compounds having 5-lipoxygenase inhibitory activity.

The compounds used in the present invention are compounds of formula (I):

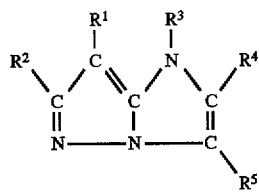

in which:

$R^1$ and $R^2$ are independently selected from the group consisting of: hydrogen atoms; $C_1$–$C_{25}$ alkyl groups; substituted $C_1$–$C_6$ alkyl groups having at cycloalkyl groups; $C_2$–$C_6$ alkenyl groups; aralkyl least one substituent selected from the group consisting of substituents (a), defined below; $C_3$–$C_8$ groups in which the or each alkyl part is $C_1$–$C_4$ and the aryl part is $C_6$–$C_{10}$ and is unsubstituted or has at least one substituent selected from the group consisting of substituents (b), defined below; arylalkenyl groups in which the aryl part is a $C_6$–$C_{10}$ aryl group which is unsubstituted or has at least one substituent selected from the group consisting of substituents (b), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b), defined below; aromatic heterocyclic groups which have from 5 to 8 ring atoms of which from 1 to 3 are hetero-atoms selected from the group consisting of nitrogen, oxygen and sulfur hetero-atoms, said group being unsubstituted or having at least one substituent selected from the group consisting of substituents (b), defined below, and being monocyclic or being fused to a benzene ring; cyano groups; and halogen atoms;

$R^3$ represents: a hydrogen atom; a $C_1$–$C_{25}$ alkyl group; a substituted $C_1$–$C_6$ alkyl group having at least one substituent selected from the group consisting of substituents (a), defined below; an aralkyl group in which the or each alkyl part is $C_1$–$C_4$ and the aryl part is $C_6$–$C_{10}$ and is unsubstituted or has at least one substituent selected from the group consisting of substituents (b), defined below; a $C_1$–$C_6$ aliphatic carboxylic acyl group; or an aromatic carboxylic acyl group in which the aryl part is a $C_6$–$C_{10}$ carbocyclic aryl group which is unsubstituted or has at least one substituent selected from the group consisting of substituents (b), defined below;

$R^4$ and $R^5$ are independently selected from the group consisting of: hydrogen atoms; $C_1$–$C_{25}$ alkyl groups; substituted $C_1$–$C_6$ alkyl groups having at least one substituent selected from the group consisting of substituents (a), defined below; $C_3$–$C_8$ cycloalkyl groups; $C_2$–$C_6$ alkenyl groups; aralkyl groups in which the alkyl part is $C_1$–$C_4$ and the or each aryl part is $C_6$–$C_{10}$ and is unsubstituted or has at least one substituent selected from the group consisting of substituents (b), defined below; arylalkenyl groups in which the aryl part is a $C_6$–$C_{10}$ aryl group which is unsubstituted or has at least one substituent selected from the group consisting of substituents (b), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b), defined below; and aromatic heterocyclic groups which have from 5 to 8 ring atoms of which from 1 to 3 are hetero-atoms selected from the group consisting of nitrogen, oxygen and sulfur hetero-atoms, said group being unsubstituted or having at least one substituent selected from the group consisting of substituents (b), defined below, and being monocyclic or being fused to a benzene ring;

substituents (a):

hydroxy groups, halogen atoms, carboxy groups, cyano groups. $C_2$–$C_7$ alkoxycarbonyl groups and aromatic heterocyclic groups which have from 5 to 8 ring atoms of which from 1 to 3 are hereto-atoms selected from the group consisting of nitrogen, oxygen and sulfur hetero-atoms, said group being unsubstituted or having at least one substituent selected from the group consisting of substituents (b), defined below, and being monocyclic or being fused to a benzene ring;

substituents (b):

$C_1$–$C_6$ alkyl groups; halogen atoms; $C_1$–$C_6$ alkoxy groups; aryloxy groups in which the aryl part is an unsubstituted $C_6$–$C_{10}$ carbocyclic aryl group; aralkyloxy groups in which the alkyl part is $C_1$–$C_4$ and the or each aryl part is $C_6$–$C_{10}$ and is unsubstituted; $C_1$–$C_6$ aliphatic carboxylic acyl groups; aromatic carboxylic acyl groups in which the aryl part is a $C_6$–$C_{10}$ carbocyclic aryl group which $C_1$–$C_6$ aliphatic carboxylic acyloxy groups; is unsubstituted or has at least one substituent selected from the group consisting of $C_1$–$C_4$ alkyl groups, $C_1$–$C_4$ alkoxy groups and halogen atoms; $C_1$–$C_6$ aliphatic carboxylic acylamino groups; aromatic carboxylic acyloxy groups in which the aryl part is a $C_6$–$C_{10}$ carbocyclic aryl group which is unsubstituted or has at least one substituent selected from the group consisting of $C_1$–$C_4$ alkyl groups, $C_1$–$C_6$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; aromatic carboxylic acylamino groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms; $C_1$–$C_4$haloalkyl groups; carbamoyl groups; alkylcarbamoyl and dialkylcarbamoyl groups in which the or each alkyl group is $C_1$–$C_4$; carboxy groups; hydroxy groups; cyano groups; and $C_2$–$C_7$ alkoxycarbonyl groups;

and pharmaceutically acceptable salts thereof.

Of these, the compounds are new and are claimed per se except those in which $R^1$ represents a hydrogen atom and $R^2$ represents an unsubstituted alkyl group or an aryl group, or in which R represents a halogen atom and $R^2$ represents a hydrogen atom, an unsubstituted alkyl group or a cycloalkyl group, or in which $R^1$ represents an unsubstituted alkyl group and $R^2$ represents an unsubstituted alkyl group.

The invention also provides a method for the treatment or prophylaxis of a disease or disorder selected from the group consisting of pain, inflammation and ulcers, by the administration to a mammal suffering from said disease or disorder of an effective amount of an active compound, wherein said active compound is selected from the group consisting of compounds of formula (I) and pharmaceutically acceptable salts thereof.

The invention still further provides a method of relieving or alleviating allergic reactions by the administration to a mammal suffering from said allergic reaction of an effective amount of an inhibitor of 5-lipoxygenase, wherein said inhibitor is selected from the group consisting of compounds of formula (I) and pharmaceutically acceptable salts thereof.

The invention also provides a pharmaceutical composition for the treatment or prophylaxis of pain, inflammation, ulcers or allergic reactions, which composition comprises an effective amount of an active compound in admixture with a pharmaceutically acceptable carrier or diluent, wherein said active compound is selected from the group consisting of compounds of formula (I) and pharmaceutically acceptable salts thereof.

The invention also provides processes for the preparation of the compounds of the present invention, which are described in greater detail hereafter.

DETAILED DESCRIPTION OF INVENTION

In the compounds of the present invention, where $R^1$, $R^2$, $R^3$, $R^4$ or $R^5$ represents an alkyl group, this may be a straight or branched chain alkyl group containing from 1 to 25 carbon atoms, preferably from 1 to 6 carbon atoms, and more preferably from 1 to 4 carbon atoms, and examples include the methyl, ethyl, propyl, isopropyl, butyl, isobutyl, sec-butyl, t-butyl, pentyl, isopentyl, neopentyl, t-pentyl, 2-methylbutyl, hexyl, isohexyl, 2-methylpentyl, hexyl, isohexyl, 1-methylpentyl, 2-methylpentyl, 3-methylpentyl, heptyl, 1-methylhexyl, 2-methylhexyl, 5-methylhexyl, 3-ethylpentyl, octyl, 2-methylheptyl, 5-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosyl, tricosyl, tetracosyl and pentacosyl groups. Of these, we generally prefer the methyl, ethyl, propyl, butyl, pentyl, isopentyl, hexyl, isohexyl, heptyl, octyl, nonyl, undecyl, tridecyl, pentadecyl, heptadecyl, nonadecyl and pentacosyl groups, of which the methyl, ethyl, propyl and butyl groups are more preferred. In the case of $R^1$ and $R^2$, the methyl and ethyl groups are generally the most preferred alkyl groups where the compound is for analgesic, anti-inflammatory and anti-ulcer use, and $C_4$–$C_{11}$ alkyl groups are generally the most preferred where the compound is for use as an inhibitor of 5-lipoxygenase.

Where $R^1$, $R^2$, $R^3$, $R^4$ or $R^5$ represents a substituted alkyl group, this has at least one substituent selected from the group consisting of substituents (a), defined above and exemplified below. Examples of the alkyl group are the $C_1$–$C_6$ groups of those given as examples above for unsubstituted alkyl groups. There is no restriction, in principle, on the number of substituents (a) which may be present on any alkyl group represented by $R^1$, $R^2$, $R^3$, $R^4$ or $R^5$, except such as may be imposed by the number of substitutable positions and, possibly, by steric constraints. In general, the maximum preferred number of substituents on any alkyl group is 3, but this may be exceeded in any specific case.

Examples of the groups and atoms which may be included within substituents (a) include:

the hydroxy, carboxy and cyano groups;

halogen atoms, such as the fluorine, chlorine, bromine and iodine atoms;

$C_2$–$C_7$ alkoxycarbonyl groups (i.e. the alkoxy part has from 1 to 6 carbon atoms), such as the methoxycarbonyl, ethoxycarbonyl, propoxycarbonyl, isopropoxycarbonyl, butoxycarbonyl, sec-butoxycarbonyl, t-butoxycarbonyl, pentyloxycarbonyl, isopentyloxycarbonyl, neopentyloxycarbonyl, t-pentyloxycarbonyl, hexyloxycarbonyl and isohexyloxycarbonyl groups;

aromatic heterocyclic groups which have from 5 to 8 ring atoms of which from 1 to 3 are hetero-atoms selected from the group consisting of nitrogen, oxygen and sulfur hereto-atoms, said group being unsubstituted or having at least one substituent selected from the group consisting of substituents (b), defined and exemplified below, and being monocyclic or being fused to a benzene ring; such substituents and the substituted groups derived from them are discussed in more detail hereafter.

Examples of substituted alkyl groups include: groups having a hydroxy substituent, such as the hydroxymethyl, 2-hydroxyethyl, 3-hydroxypropyl and 2-hydroxypropyl groups; groups having at least one halogen substituent, such as the fluoromethyl, trifluoromethyl, 2-fluoroethyl, 2,2,2-trifluoroethyl, 3-fluoropropyl, 4-fluorobutyl, 5-fluoropentyl, 6-fluorohexyl, chloromethyl, trichloromethyl, 2-chloroethyl, 2,2,2-trichloroethyl, 3-chloropropyl, 4-chlorobutyl, 5-chloropentyl, 6-chlorohexyl, iodomethyl, 2-iodoethyl, 3-iodopropyl, 4-iodobutyl, 5-iodopentyl, 6-iodohexyl, bromomethyl, tribromomethyl, 2-bromoethyl, 2,2,2-tribromoethyl, 3-bromopropyl, 4-bromobutyl, 5-bromopentyl and 6-bromohexyl groups; groups having a cyano substituent, such as the cyanomethyl, 2-cyanoethyl, 1-cyanoethyl, 3-cyanopropyl, 2-cyanopropyl, 4-cyanobutyl, 5-cyanopentyl and 6-cyanohexyl groups; groups having a carboxy substituent, such as the carboxymethyl, 2-carboxyethyl, 1-carboxyethyl, 3-carboxypropyl, 4-carboxybutyl, 5-carboxypentyl and 6-carboxyhexyl groups; and groups having an alkoxycarbonyl substituent, such as the methoxycarbonylmethyl, ethoxycarbonylmethyl, 2-ethoxycarbonylethyl, 3-methoxycarbonylpropyl, 4-ethoxycarbonylbutyl, 3-propoxycarbonylbutyl, 5-methoxycarbonylpentyl, 2-propoxycarbonylpentyl, 5-t-butoxycarbonylpentyl, 6-methoxycarbonylhexyl and 6-ethoxycarbonylhexyl groups.

Where $R^1$, $R^2$, $R^4$ or $R^5$ represents a cycloalkyl group, this has from 3 to 8 ring carbon atoms, and examples include the cyclopropyl, cyclobutyl, cyclopentyl, cyclohexyl, cycloheptyl and cyclooctyl groups, of which the cyclopropyl, cyclopentyl and cyclohexyl groups are preferred.

Where $R^1$, $R^2$, $R^4$ or $R^5$ represents an alkenyl group, this has from 2 to 6, preferably 3 or 4, carbon atoms and may be a straight or branched chain group. Examples include the vinyl, allyl, 1-propenyl, 2-butenyl, 1-butenyl, 2-methylallyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the allyl, 2-butenyl and 2-methylallyl groups are preferred.

Where $R^1$, $R^2$, $R^3$, $R^4$ or $R^5$ represents an aralkyl group, the alkyl part is $C_1$–$C_4$ and the or each aryl part is $C_6$–$C_{10}$ and is unsubstituted or has at least one substituent selected from the group consisting of substituents (b), defined and exemplified below. The number of aryl groups is normally from 1 to 3, although this is not critical. Examples of such alkyl groups include those alkyl groups having from 1 to 4 carbon atoms and exemplified above in relation to the alkyl groups that may be represented by $R^1$ etc. Examples of the aryl groups include the phenyl, 1-naphthyl and 2-naphthyl groups, and these may be substituted or unsubstituted. Preferred unsubstituted aralkyl groups include the benzyl, phenethyl, 1-phenylethyl, benzhydryl, triphenylmethyl, 2-phenylpropyl, 3-phenylpropyl, 4-phenylbutyl, 1-naphthylmethyl and 2-naphthylmethyl groups. Such groups may also have at least one, and preferably from 1 to 3, of substituents (b), defined and exemplified below.

Examples of substituents (b) include:

$C_1$–$C_6$ alkyl groups, such as the methyl, ethyl, propyl, isopropyl, butyl, isobutyl, sec-butyl, t-butyl, pentyl, isopentyl, neopentyl, t-pentyl, 2-methylbutyl, hexyl and isohexyl groups;

halogen atoms, especially the chlorine, fluorine, bromine and iodine atoms;

$C_1$–$C_6$ alkoxy groups, such as the methoxy, ethoxy, propoxy, isopropoxy, butoxy, isobutoxy, sec-butoxy, t-butoxy, pentyloxy, isopentyloxy, neopentyloxy, t-pentyloxy, 2-methylbutoxy, hexyloxy and isohexyloxy groups;

aryloxy groups in which the aryl part is an unsubstituted $C_6$–$C_{10}$ carbocyclic aryl group, such as the phenoxy, 1-naphthyloxy and 2-naphthyloxy groups;

aralkyloxy groups in which the alkyl part is $C_1$–$C_4$ and the aryl part is $C_6$–$C_{10}$ and is unsubstituted, such as the benzyloxy, phenethyloxy, 1-phenylethoxy, 3-phenylpropoxy, 4-phenylbutoxy, 1-naphthylmethoxy and 2-naphthylmethoxy groups;

$C_1$–$C_6$ aliphatic carboxylic acyl groups, such as the formyl, acetyl, propionyl, butyryl, isobutyryl, valeryl, isovaleryl, pivaloyl, hexanoyl, acryloyl, methacryloyl, propioloyl, crotonoyl and isocrotonoyl groups;

aromatic carboxylic acyl groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms, such as the benzoyl, naphthoyl, toluoyl (o-, m- or p-), 2,4,6-trimethylbenzoyl, chlorobenzoyl (o-, m- or p-) and methoxybenzoyl (o-, m- or p-) groups;

$C_1$–$C_6$ aliphatic carboxylic acyloxy groups, such as the formyloxy, acetyloxy, propionyloxy, butyryloxy, isobutyryloxy, valeryloxy, isovaleryloxy, pivaloyloxy, hexanoyloxy, acryloyloxy, methacryloyloxy, propioloyloxy, crotonoyloxy and isocrotonoyloxy groups;

aromatic carboxylic acyloxy groups in which the aryl part is a $C_6$–$C_{10}$ carbocyclic aryl group which alkyl groups, $C_1$–$C_4$ alkoxy groups and halogen is unsubstituted or has at least one substituent selected from the group consisting of $C_1$–$C_4$ atoms, such as the benzoyloxy, naphthoyloxy, toluoyloxy (o-, m- or p-), 2,4,6-trimethylbenzoyloxy, chlorobenzoyloxy (o-, m- or p-) and methoxybenzoyloxy (o-, m- or p-) groups;

amino groups;

$C_1$–$C_4$ alkylamino groups and dialkylamino groups in which each alkyl part is $C_1$–$C_4$, such as the methylamino, ethylamino, propylamino, isopropylamino, butylamino, isobutylamino, sec-butylamino, t-butylamino, dimethylamino, diethylamino, dipropylamino, dibutylamino, methylethylamino, methylbutylamino and ethylbutylamino groups;

$C_1$–$C_6$ aliphatic carboxylic acylamino groups, such as the formylamino, acetylamino, propionylamino, butyrylamino, isobutyrylamino, valerylamino, isovalerylamino, pivaloylamino, hexanoylamino, acryloylamino, methacryloylamino, propioloylamino, crotonoylamino and isocrotonoylamino groups;

aromatic carboxylic acylamino groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms, such as the benzoylamino, naphthoylamino, toluoylamino (o-, m- or p-), 2,4,6-trimethylbenzoylamino, chlorobenzoylamino (o-, m- or p-) and methaminobenzoylamino (o-, m- or p-) groups;

$C_1$–$C_4$ haloalkyl groups, such as the trifluoromethyl, 2,2,2-trichloroethyl, 2-haloethyl (e.g. 2-chloroethyl, 2-fluoroethyl, 2-bromoethyl or 2-iodoethyl), 2,2-dibromoethyl, 2,2,2-tribromoethyl, 4-chlorobutyl, 4-bromobutyl and 4-fluorobutyl groups;

carbamoyl groups;

alkylcarbamoyl and dialkylcarbamoyl groups in which the or each alkyl group is $C_1$–$C_4$, such as the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, dimethylcarbamoyl, diethylcarbamoyl, dipropylcarbamoyl, dibutylcarbamoyl, methylethylcarbamoyl, methylbutylcarbamoyl and ethylbutylcarbamoyl groups;

carboxy groups; and $C_2$–$C_7$ alkoxycarbonyl groups (i.e. the alkoxy part has from 1 to 6, preferably from 1 to 4, carbon atoms), such as the methoxycarbonyl, ethoxycarbonyl, propoxycarbonyl, isopropoxycarbonyl, butoxycarbonyl, sec-butoxycarbonyl, t-butoxycarbonyl, pentyloxycarbonyl, isopentyloxycarbonyl, neopentyloxycarbonyl, t-pentyloxycarbonyl, hexyloxycarbonyl and isohexyloxycarbonyl groups.

Where $R^1$, $R^2$, $R^4$ or $R^5$ represents an arylalkenyl group, the aryl part is a $C_6$–$C_{10}$ aryl group which is unsubstituted or has at least one substituent selected from the group consisting of substituents (b), defined and exemplified above, and the alkenyl part is a $C_2$–$C_3$ alkenyl group. Examples of aryl groups are as given in relation to the aryl groups forming part of an aralkyl group. Examples of alkenyl groups include the vinyl, 1-propenyl and 2-propenyl groups, and the aryl group may be a substituent on any carbon atom of these alkenyl groups. Examples of such arylalkenyl groups include the styryl, α-methylstyryl, cinnamyl, 3-(1-naphthyl)-2-propenyl and 3-phenyl-1-propenyl groups and such groups having on the aryl part at least one substituent selected from the group consisting of substituents (b).

Where $R^1$, $R^2$, $R^4$ or $R^5$ represents an aryl group, this has from 6 to 10 ring carbon atoms and may be unsubstituted or may have at least one substituent selected from the group consisting of substituents (b), defined and exemplified above. Preferred unsubstituted aryl groups include the phenyl, 1-naphthyl and 2-naphthyl groups. Preferred substituents are as exemplified above. Preferred examples of substituted and unsubstituted groups include: the unsubstituted groups, such as the phenyl, 2-naphthyl and 1-naphthyl groups; the halogen-substituted groups, such as the p-fluorophenyl, o-fluorophenyl, m-fluorophenyl, p-bromophenyl, m-bromophenyl, o-chlorophenyl, p-chlorophenyl, m-chlorophenyl and 3,4-dichlorophenyl groups; the haloalkyl-substituted groups, such as the p-trifluoromethylphenyl, m-trifluoromethylphenyl and o-trifluoromethylphenyl groups; the alkyl-substituted groups, such as the p-tolyl, m-tolyl and o-tolyl groups; the alkoxy-substituted groups, such as the p-methoxyphenyl, m-methoxyphenyl, o-methoxyphenyl and 3,4-dimethoxyphenyl groups; the amino-substituted groups, such as the p-aminophenyl group; the aryloxy-substituted groups, such as the p-phenoxyphenyl group; the aralkyloxy-substituted groups, such as the p-benzyloxyphenyl, m-benzyloxyphenyl and o-benzyloxyphenyl groups; the hydroxy-substituted groups; such as the p-hydroxyphenyl, o-hydroxyphenyl and m-hydroxyphenyl groups; the cyano-substituted groups, such as the p-cyanophenyl group; the acyl-substituted groups, such as the p-benzoylphenyl group; the carboxy-substituted groups, such as the p-carboxyphenyl group; the carbamoyl-substituted groups, such as the p-carbamoylphenyl group; and the alkoxycarbonyl-substituted groups, such as the p-methoxycarbonylphenyl and p-ethoxycarbonylphenyl groups.

Where $R^1$, $R^2$, $R^4$ or $R^5$ or substituent (a) represents an aromatic heterocyclic group, this has from 5 to 8, preferably 5 or 6, ring atoms of which from 1 to 3 are hereto-atoms selected from the group consisting of nitrogen, oxygen and sulfur hereto-atoms. More preferably, the heterocyclic group has from 1 to 3 hetero-atoms, of which 0 or from 1 to 3 may be nitrogen atoms and 0, 1 or 2 may be sulfur and/or oxygen atoms (provided, of course, that the total does not exceed 3). An aromatic heterocyclic group is a heterocyclic group having an aromatic arrangement of double bonds. The group may be unsubstituted or may have at least one substituent selected from the group consisting of substituents (b), defined below, and it may be monocyclic or it may be fused to a benzene ring. Examples of unsubstituted heterocyclic groups include the thienyl (e.g. 2-thienyl or 3-thienyl), furyl (e.g. 2-furyl), pyranyl, pyrrolyl, imidazolyl, pyrazolyl (e.g. 3-pyrazolyl), thiazolyl, isothiazolyl, triazolyl, oxazolyl, isoxazolyl, pyridyl (e.g. 2-pyridyl, 3-pyridyl or 4-pyridyl), pyrazinyl, pyrimidinyl, pyridazinyl, furazanyl, pyrrolidinyl, pyrrolinyl, imidazolidinyl, imidazolinyl, pyrazolidinyl, pyrazolinyl, piperidyl (e.g. piperidino and 4-piperidyl), piperazinyl, morpholinyl, thiomorpholinyl, azepinyl, azocinyl, triazocinyl, benzofuranyl, isobenzofuranyl, chromenyl, indolyl, isoindolyl, quinolyl, isoquinolyl, naphthyridinyl, quinoxalinyl, quinazolinyl, cinnolinyl, chromanyl, isochromanyl, indolinyl and isoindolinyl groups. Examples of such substituted heterocyclic groups include the 6-methyl-3-pyridyl, 2,6-dichloro-4-pyridyl, 2-methoxy-3-pyridyl, 6-methyl-2-pyridyl, 6-chloro-3-pyridyl, 6-(trifluoromethyl)-3-pyridyl, 5-chloro-2-pyridyl, 5-(trifluoromethyl)-2-furyl, 5-methyl-2-furyl, 2,5-dimethyl-3-furyl, 5-(trifluoromethyl)-2-thienyl, 3-methyl-2-thienyl, 5-methyl- 2-thienyl, 5-chloro-2-thienyl, 1-methyl-2-pyrrolyl, 1,5-dimethyl-2-pyrrolyl, 3,5-dimethyl-2-pyrrolyl, 4-methyl-5-imidazolyl, 4-methyl-5-oxazolyl, 4-pyrazolyl, 5-methyl-4-pyrazolyl, 1-methyl-2-indolyl, 5-methoxy-2-indolyl, 5-chloro-2-indolyl, isoquinolyl (e.g. 1-isoquinolyl), and quinolyl (e.g. 2-quinolyl) groups.

Where $R^1$, $R^2$, $R^4$ or $R^5$ represents a heterocyclic-substituted alkyl group, the heterocyclic part may be any one of the heterocyclic groups defined and exemplified above, and the alkyl part may be any one of the alkyl groups having from 1 to 6 carbon atoms referred to above, preferably a $C_1$ or $C_2$ group, i.e. a methyl or ethyl group. Specific examples of such heterocyclic-substituted alkyl groups include the furfuryl, 2-(2-furyl)ethyl, 2-thenyl, 2-(2-thienyl)ethyl, 3-(2-thienyl)propyl, 2-imidazolylmethyl, 2-thiazolylmethyl, 2-oxazolylmethyl, 5-isoxazolylmethyl, 2-pyridylmethyl, 3-pyridylmethyl, 2-(3-pyridyl)ethyl, 3-(3-pyridyl)propyl and 3-indolylmethyl groups, where the heterocyclic part may be unsubstituted or may have at least one substituent selected from the group consisting of substituents (b), defined and exemplified above.

Where $R^3$ represents an aliphatic carboxylic acyl group, this has from 1 to 6 carbon atoms. The acyl group may have a saturated or unsaturated carbon chain. In the case of a saturated carbon chain, the group is a $C_1$–$C_6$ alkanoyl group, preferably a $C_2$–$C_4$ alkanoyl group; in the case of an unsaturated carbon chain, the group is a $C_3$–$C_6$ alkenoyl or alkynoyl group, preferably an alkenoyl group, and it may have one or more carbon—carbon double or triple bonds. Examples of such aliphatic carboxylic acyl groups include the acetyl, propionyl, butyryl, isobutyryl, 2-methylpropionyl, pentanoyl, 2-methylbutyryl, pivaloyl, valeryl, isovaleryl, hexanoyl, 2-methylpentanoyl, 3-methylpentanoyl, 4-methylpentanoyl, acryloyl, propioloyl, methacryloyl, crotonoyl and isocrotonoyl groups.

Where $R^3$ represents an aromatic carboxylic acyl group, the aryl part of the group is a $C_6$–$C_{10}$ carbocyclic aryl group which is unsubstituted or has at least one substituent selected from the group consisting of substituents (b), defined and exemplified above. Examples of such groups include the benzoyl, 1-naphthoyl and 2-naphthoyl groups, as well as such groups having one or more of the substituents defined above, such as the o-, m- or p-toluoyl, o-, m- or p-anisoyl, and o-, m- or p-chlorobenzoyl groups.

In general, where substituents are referred to above, there is no restriction on the number of such substituents, except, as specifically explained in relation to substituents on aryl groups, those that might arise as a result of the number of substitutable positions on the group bearing the substituent (s), and possibly also steric constraints. Although the exact number of substituents permissible may, therefore, vary in a manner well known to those skilled in the art, as a general rule, from 1 to 3 such substituents are preferred, except where otherwise indicated herein.

Preferred classes of compounds of the present invention consist of:

(A) those compounds of formula (I) in which:
$R^1$ and $R^2$ are independently selected from the group consisting of: hydrogen atoms; $C_1$–$C_{11}$ alkyl groups; substituted $C_1$–$C_6$ alkyl groups having at least one substituent selected from the group consisting of substituents (a), defined below; $C_3$–$C_6$ cycloalkyl groups; $C_2$–$C_6$ alkenyl groups; aralkyl groups in which the alkyl part is $C_1$–$C_4$ and the aryl part is a phenyl group which is unsubstituted or has at least one substituent selected from the group consisting of substituents ($b^1$), defined below; phenylalkenyl groups in which the phenyl part is unsubstituted or has at least one substituent selected from the group consisting of substituents ($b^1$), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents ($b^1$), defined below; aromatic heterocyclic groups which have 5 or 6 ring atoms of which from 1 to 3 are hetero-atoms selected from the group consisting of nitrogen, oxygen and sulfur hetero-atoms, said group being unsubstituted or having at least one substituent selected from the group consisting of substituents ($b^1$), defined below, and being monocyclic or being fused to a benzene ring; and halogen atoms;

(B) those compounds of formula (I) in which:
$R^3$ represents: a hydrogen atom; a $C_1$–$C_{11}$ alkyl group; a substituted $C_1$–$C_6$ alkyl group having at least one substituent selected from the group consisting of substituents ($a^1$), defined below; an aralkyl group in which the alkyl part is $C_1$–$C_4$ and the aryl part is a phenyl group which is unsubstituted or has at least one substituent selected from the group consisting of substituents ($b^1$), defined below; a $C_1$–$C_6$ aliphatic carboxylic acyl group; or a benzoyl group which is unsubstituted or has at least one substituent selected from the group consisting of substituents ($b^1$), defined below;

(C) those compounds of formula (I) in which:
$R^4$ and $R^5$ are independently selected from the group consisting of: hydrogen atoms; $C_1$–$C_{11}$ alkyl groups; substituted $C_1$–$C_6$ alkyl groups having at least one substituent selected from the group consisting of substituents ($a^1$), defined below; $C_3$–$C_6$ cycloalkyl groups; $C_2$–$C_6$ alkenyl groups; aralkyl groups in which the alkyl part is $C_1$–$C_4$ and the aryl part is a phenyl group which is unsubstituted or has at least one substituent selected from the group consisting of substituents ($b^1$), defined below; phenylalkenyl groups in which the phenyl part is unsubstituted or has at least one substituent selected from the group consisting of substituents ($b^1$), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents ($b^1$), defined below; and aromatic heterocyclic groups which have 5 or 6 ring atoms of which from 1 to 3 are hereto-atoms selected from the group consisting of nitrogen, oxygen and sulfur hereto-atoms, said group being unsubstituted or having at least one substituent selected from the group consisting of substituents ($b^1$), defined below, and being monocyclic or being fused to a benzene ring;

substituents ($a^1$):
hydroxy groups, halogen atoms, carboxy groups, cyano groups, $C_2$–$C_4$ alkoxycarbonyl groups and aromatic heterocyclic groups which have 5 or 6 ring atoms of which from 1 to 3 are hereto-atoms selected from the group consisting of nitrogen, oxygen and sulfur hetero-atoms, said group being unsubstituted or having at least one substituent selected from the group consisting of substituents ($b^1$), defined below, and being monocyclic or being fused to a benzene ring;

substituents ($b^1$):
$C_1$–$C_4$ alkyl groups; halogen atoms; $C_1$–$C_4$ alkoxy groups; phenoxy groups; aralkyloxy groups in which the alkyl part is $C_1$–$C_4$ and the aryl part is an unsubstituted phenyl group; $C_2$–$C_6$ aliphatic carboxylic acyl groups; benzoyl groups which are unsubstituted or have at least one substituent selected from the group consisting of $C_1$–$C_4$ alkyl groups, $C_1$–$C_4$ alkoxy groups and halogen atoms; $C_1$–$C_6$ aliphatic carboxylic acyloxy groups; benzoyloxy groups which are unsubstituted or have at least one substituent selected from the group consisting of $C_1$–$C_4$ alkyl groups, $C_1$–$C_4$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; benzoylamino groups which are unsubstituted or have at least one substituent selected from the group consisting of $C_1$–$C_4$ alkyl groups, $C_1$–$C_4$ alkoxy groups and halogen atoms; $C_1$–$C_4$ haloalkyl groups; carbamoyl groups; alkylcarbamoyl and dialkylcarbamoyl groups in which the or each alkyl group is $C_1$–$C_4$; carboxy groups; and $C_2$–$C_5$ alkoxycarbonyl groups;

and pharmaceutically acceptable salts thereof.

Especially preferred are those compounds in which $R^1$ and $R^2$ are as defined in (A) above, $R^3$ is as defined in (B) above and $R^4$ and $R^5$ are as defined in (C) above.

More preferred compounds of the present invention are those compounds of formula (I) in which:
$R^1$ and $R^2$ are independently selected from the group consisting of: hydrogen atoms; $C_1$–$C_6$ alkyl groups; substituted $C_1$–$C_4$ alkyl groups having at least one substituent selected from the group consisting of substituents ($a^2$), defined below; benzyl groups in which the phenyl part is unsubstituted or has at least one substituent selected from the group consisting of substituents (b²), defined below; cinnamyl groups; phenyl groups; naphthyl groups; phenyl or naphthyl groups having at least one substituent selected from the group consisting of substituents (b²), defined below; aromatic heterocyclic groups which have 5 or 6 ring atoms of which 1 or 2 is a hereto-atom selected from the group consisting of nitrogen, oxygen and sulfur hetero-atoms, said group being unsubstituted or having at least one substituent selected from the group consisting of substituents (b²), defined below; and halogen atoms;

$R^3$ represents: a hydrogen atom; a $C_1$–$C_6$ alkyl group; a substituted $C_1$–$C_4$ alkyl group having at least one substituent selected from the group consisting of substituents (a²), defined below; a benzyl group which is unsubstituted or has at least one substituent selected from the group consisting of substituents (b²), defined below; a $C_2$–$C_4$ aliphatic carboxylic acyl group; or a benzoyl group which is unsubstituted or has at least one substituent selected from the group consisting of substituents (b²), defined below;

$R^4$ and $R^5$ are independently selected from the group consisting of: hydrogen atoms; $C_1$–$C_6$ alkyl groups; substituted $C_1$–$C_4$ alkyl groups having at least one substituent selected from the group consisting of substituents (a²), defined below; benzyl groups which are unsubstituted or have at least one substituent selected from the group consisting of substituents (b²), defined below; cinnamyl groups; phenyl groups; naphthyl groups; phenyl or naphthyl groups having at least one substituent selected from the group consisting of substituents (b²), defined below; and aromatic heterocyclic groups which have 5 or 6 ring atoms of which 1 or 2 is a hereto-atom selected from the group consisting of nitrogen, oxygen and sulfur hetero-atoms, said group being unsubstituted or having at least one substituent selected from the group consisting of substituents (b²), defined below;

substituents (a²):

hydroxy groups, halogen atoms, cyano groups, carboxy groups, $C_2$–$C_4$ alkoxycarbonyl groups and aromatic heterocyclic groups which have 5 or 6 ring atoms of which 1 or 2 is a hereto-atom selected from the group consisting of nitrogen, oxygen and sulfur hetero-atoms, said group being unsubstituted or having at least one substituent selected from the group consisting of substituents (b²), defined below;

substituents (b²):

$C_1$–$C_4$ alkyl groups; halogen atoms; $C_1$–$C_4$ alkoxy groups; trifluoromethyl groups; hydroxy groups; cyano groups; amino groups; carbamoyl groups; phenoxy groups; $C_2$–$C_6$ aliphatic carboxylic acyl groups; benzoyl groups which are unsubstituted or have at least one substituent selected from the group consisting of $C_1$–$C_2$ alkyl groups, $C_1$–$C_2$ alkoxy groups and halogen atoms; $C_2$–$C_4$ aliphatic carboxylic acyloxy groups; benzoyloxy groups which are unsubstituted or have at least one substituent selected from the group consisting of $C_1$–$C_2$ alkyl groups, $C_1$–$C_2$ alkoxy groups and halogen atoms; carboxy groups; and $C_2$–$C_5$ alkoxycarbonyl groups;

and pharmaceutically acceptable salts thereof.

A still more preferred class of compounds of the present invention are those compounds of formula (I) in which:

$R^1$ represents a hydrogen atom or a $C_1$–$C_6$ alkyl group;

$R^2$ represents: a phenyl group; a substituted phenyl group having at least one substituent selected from the group consisting of substituents (b²), defined above; or an aromatic heterocyclic group which has 5 or 6 ring atoms of which 1 is a hereto-atom selected from the group consisting of nitrogen, oxygen and sulfur hetero-atoms, said group being unsubstituted or having at least one substituent selected from the group consisting of substituents (b²), defined above;

$R^3$ represents: a hydrogen atom; a $C_1$–$C_4$ alkyl group; a substituted $C_1$–$C_4$ alkyl group having at least one substituent selected from the group consisting of substituents (a), defined above; a $C_2$–$C_4$ aliphatic carboxylic acyl group; or a benzoyl group which is unsubstituted or has at least one substituent selected from the group consisting of substituents (b²), defined below;

$R^4$ and $R^5$ are independently selected from the group consisting of: hydrogen atoms; $C_1$–$C_6$ alkyl groups; substituted $C_1$–$C_4$ alkyl groups having at least one substituent selected from the group consisting of substituents (a²), defined above; and aromatic heterocyclic groups which have 5 or 6 ring atoms of which 1 is a hetero-atom selected from the group consisting of nitrogen, oxygen and sulfur hetero-atoms, said group being unsubstituted or having at least one substituent selected from the group consisting of substituents (b²), defined above;

and pharmaceutically acceptable salts thereof.

An alternative still more preferred class of compounds of the present invention are those compounds of formula (I) in which:

$R^1$ represents: a phenyl group; a substituted phenyl group having at least one substituent selected from the group consisting of substituents (b²), defined above; or an aromatic heterocyclic group which has 5 or 6 ring atoms of which 1 is a hetero-atom selected from the group consisting of nitrogen, oxygen and sulfur hetero-atoms, said group being unsubstituted or having at least one substituent selected from the group consisting of substituents (b²), defined above;

$R^2$ represents a hydrogen atom or a $C_1$–$C_6$ alkyl group;

$R^3$ represents: a hydrogen atom; a $C_1$–$C_4$ alkyl group; a substituted $C_1$–$C_4$ alkyl group having at least one substituent selected from the group consisting of substituents (a²), defined above; a $C_2$–$C_4$ aliphatic carboxylic acyl group; or a benzoyl group which is unsubstituted or has at least one substituent selected from the group consisting of substituents (b²), defined below;

$R^4$ and $R^5$ are independently selected from the group consisting of: hydrogen atoms; $C_1$–$C_6$ alkyl groups; substituted $C_1$–$C_4$ alkyl groups having at least one substituent selected from the group consisting of substituents (a²), defined above; and aromatic heterocyclic groups which have 5 or 6 ring atoms of which 1 is a hereto-atom selected from the group consisting of nitrogen, oxygen and sulfur hetero-atoms, said group being unsubstituted or having at least one substituent selected from the group consisting of substituents (b²), defined above;

and pharmaceutically acceptable salts thereof.

One most preferred class of compounds of the present invention are those compounds of formula (I) in which:

$R^1$ represents a hydrogen atom or a methyl or ethyl group;

$R^2$ represents: a phenyl group; a substituted phenyl group having at least one substituent selected from the group consisting of methyl groups, chlorine atoms, trifluoromethyl groups and methoxy groups; a thienyl group; a furyl group; or a thienyl or furyl group having at least one substituent selected from the group consisting of methyl groups, methoxy groups, chlorine atoms and trifluoromethyl groups;

$R^3$ represents: a hydrogen atom; a $C_1$–$C_2$ alkyl group; a $C_2$–$C_4$ aliphatic carboxylic acyl group; a benzyl group; a cyanomethyl group; a ($C_1$–$C_4$ alkoxy)carbonylmethyl group; or a benzoyl group;

$R^4$ and $R^5$ are independently selected from the group consisting of: hydrogen atoms; $C_1$–$C_2$ alkyl groups; and substituted $C_1$–$C_2$ alkyl groups having at least one substituent selected from the group consisting of $C_2$–$C_3$ alkoxycarbonyl groups;

and pharmaceutically acceptable salts thereof.

Another most preferred class of compounds of the present invention are those compounds of formula (I) in which:

$R^1$ represents: a phenyl group; a substituted phenyl group having at least one substituent selected from the group consisting of methyl groups, chlorine atoms, trifluoromethyl groups and methoxy groups; a thienyl group; a furyl group; or a thienyl or furyl group having at least one substituent selected from the group consisting of methyl groups, methoxy groups, chlorine atoms and trifluoromethyl groups;

$R^2$ represents a hydrogen atom or a methyl or ethyl group;

$R^3$ represents: a hydrogen atom; a $C_1$–$C_2$ alkyl group; a benzyl group; a cyanomethyl group; a ($C_1$–$C_4$ alkoxy) carbonylmethyl group; a $C_2$–$C_4$ aliphatic carboxylic acyl group; or a benzoyl group;

$R^4$ and $R^5$ are independently selected from the group consisting of: hydrogen atoms; $C_1$–$C_2$ alkyl groups; and substituted $C_1$–$C_2$ alkyl groups having at least one substituent selected from the group consisting of $C_2$–$C_3$ alkoxycarbonyl groups;

and pharmaceutically acceptable salts thereof.

The compounds of the present invention necessarily contain basic groups and can, therefore, form acid addition salts. The nature of such salts and of the acids employed to form them is not critical to the invention, provided that, where the compound is intended for use therapeutically, the salt is pharmaceutically acceptable, which, as is well known, means that it does not have a lower (or significantly lower) activity or a higher (or significantly higher) toxicity than the free base. However, where the compound is intended for other uses, e.g. as an intermediate in the preparation of other compounds, even this limitation does not apply.

Examples of acids which can form such salts include: inorganic acids, such as hydrochloric acid, hydrobromic acid, hydroiodic acid, phosphoric acid, sulfuric acid or nitric acid; organic sulfonic acids, such as methanesulfonic acid, ethanesulfonic acid, benzenesulfonic acid or p-toluenesulfonic acid; and organic carboxylic acids, such as oxalic acid, tartaric acid, citric acid, maleic acid, malonic acid, succinic acid, acetic acid, benzoic acid, mandelic acid, ascorbic acid, lactic acid, gluconic acid and malic acid.

Specific examples of compounds of the present invention are those compounds of formula (I) in which $R^1$, $R^2$, $R^3$, $R^4$ and $R^5$ are as defined in the following Table 1. In the Table, the following abbreviations are used:

| | |
|---|---|
| Ac | acetyl |
| All | allyl |
| Boz | benzoyl |
| Bu | butyl |
| Bz | benzyl |
| Car | carbamoyl |
| Et | ethyl |
| Etc | ethoxycarbonyl |
| Fur | furyl |
| Hdc | hexadecyl |
| Hpdc | heptadecyl |
| Hx | hexyl |
| Imid | imidazolyl |
| Ind | indolyl |
| Me | methyl |
| Mec | methoxycarbonyl |
| Ndc | nonadecyl |
| Nn | nonyl |
| Np | naphthyl |
| Oc | octyl |
| Oxa | oxazolyl |
| Pdc | pentadecyl |
| Ph | phenyl |
| Pn | pentyl |
| iPn | isopentyl |
| Pr | propyl |
| iPr | isopropyl |
| Pyaz | pyrazolyl |
| Pyr | pyridyl |
| Pyrr | pyrrolyl |
| iQuin | isoquinolyl |
| Tdc | tridecyl |
| Tfm | trifluoromethyl |
| Then | thenyl |
| Thi | thienyl |
| Udc | undecyl |

TABLE 1

| Cpd No. | $R^1$ | $R^2$ | $R^3$ | $R^4$ | $R^5$ |
|---|---|---|---|---|---|
| 1 | H | Ph | H | H | H |
| 2 | H | p-FPh | H | H | H |
| 3 | H | p-TfmPh | H | H | H |
| 4 | H | m-TfmPh | H | H | H |
| 5 | H | o-TfmPh | H | H | H |
| 6 | H | p-MePh | H | H | H |
| 7 | H | m-MePh | H | H | H |
| 8 | H | o-MePh | H | H | H |
| 9 | H | p-MeOPh | H | H | H |
| 10 | H | m-MeOPh | H | H | H |
| 11 | H | o-MeOPh | H | H | H |
| 12 | H | p-BrPh | H | H | H |
| 13 | H | m-BrPh | H | H | H |
| 14 | H | o-ClPh | H | H | H |
| 15 | H | 2-ClPh | H | H | H |
| 16 | H | m-ClPh | H | H | H |
| 17 | H | 3,4-diClPh | H | H | H |
| 18 | Me | Ph | H | H | H |
| 19 | Et | Ph | H | H | H |
| 20 | iPr | Ph | H | H | H |
| 21 | Pr | Ph | H | H | H |
| 22 | Bu | Ph | H | H | H |

TABLE 1-continued

| Cpd No. | R¹ | R² | R³ | R⁴ | R⁵ |
|---|---|---|---|---|---|
| 23 | F₃CCH₂— | Ph | H | H | H |
| 24 | All | Ph | H | H | H |
| 25 | Bz | Ph | H | H | H |
| 26 | Ph | Ph | H | H | H |
| 27 | Me | p-ClPh | H | H | H |
| 28 | Et | p-ClPh | H | H | H |
| 29 | H | Bz | H | H | H |
| 30 | H | Ph | Me | H | H |
| 31 | H | m-TfmPh | Et | H | H |
| 32 | H | Ph | Ac | H | H |
| 33 | H | p-ClPh | Boz | H | H |
| 34 | H | Ph | H | Me | H |
| 35 | H | Ph | H | H | Me |
| 36 | H | Ph | H | EtcCH₂— | H |
| 37 | H | Ph | H | H | EtcCH₂— |
| 38 | Me | Ph | H | EtcCH₂— | H |
| 39 | HOCH₂— | Ph | H | H | H |
| 40 | Br | Ph | H | H | H |
| 41 | Ph | H | H | H | H |
| 42 | Me | 2-TfmPh | H | H | H |
| 43 | All | p-TfmPh | H | H | H |
| 44 | Me | m-ClPh | H | H | H |
| 45 | F₃CCH₂— | p-ClPh | H | H | H |
| 46 | All | p-ClPh | H | H | H |
| 47 | H | Ph | H | Ph | H |
| 48 | H | Ph | H | H | Ph |
| 49 | H | 1-Me-2-Ind | H | H | H |
| 50 | H | 1-Me-2-Pyrr | H | H | H |
| 51 | H | 1,5-diMe-2-Pyrr | H | H | H |
| 52 | H | 3,5-diMe-2-Pyrr | H | H | H |
| 53 | H | 2-Thi | H | H | H |
| 54 | H | 3-Me-2-Thi | H | H | H |
| 55 | H | 5-Cl-2-Thi | H | H | H |
| 56 | H | 5-Me-2-Thi | H | H | H |
| 57 | Me | 2-Thi | H | H | H |
| 58 | Et | 2-Thi | H | H | H |
| 59 | Ph | 2-Thi | H | H | H |
| 60 | H | 2-Fur | H | H | H |
| 61 | H | 5-Me-2-Fur | H | H | H |
| 62 | H | 2,5-diMe-3-Fur | H | H | H |
| 63 | H | 2-Pyr | H | H | H |
| 64 | H | 4-Pyr | H | H | H |
| 65 | H | 3-Pyr | H | H | H |
| 66 | H | 6-Me-3-Pyr | H | H | H |
| 67 | H | 2,6-diCl-4-Pyr | H | H | H |
| 68 | H | 2-MeO-3-Pyr | H | H | H |
| 69 | H | 4-Me-5-Oxa | H | H | H |
| 70 | H | 5-MeO-2-Ind | H | H | H |
| 71 | H | 5-Cl-2-Ind | H | H | H |
| 72 | H | 1-iQuin | H | H | H |
| 73 | H | 3-Pyaz | H | H | H |
| 74 | H | 4-Me-5-Imid | H | H | H |
| 75 | H | 2-Then | H | H | H |
| 76 | Ph | Me | H | H | H |
| 77 | Ph | Et | H | H | H |
| 78 | Ph | Pr | H | H | H |
| 79 | Ph | iPr | H | H | H |
| 80 | Ph | Bu | H | H | H |
| 81 | Ph | H | Me | H | H |
| 82 | Ph | H | Et | H | H |
| 83 | Ph | H | Ac | H | H |
| 84 | Ph | H | Boz | H | H |
| 85 | Ph | H | H | Me | H |
| 86 | Ph | H | H | H | Me |
| 87 | Ph | H | H | EtcCH₂— | H |
| 88 | Ph | H | H | H | EtcCH₂— |
| 89 | Ph | Me | H | EtcCH₂— | H |
| 90 | p-TfmPh | H | H | H | H |
| 91 | p-TfmPh | Me | H | H | H |
| 92 | m-TfmPh | H | H | H | H |
| 93 | m-TfmPh | Me | H | H | H |
| 94 | o-TfmPh | H | H | H | H |
| 95 | o-TfmPh | Me | H | H | H |
| 96 | p-FPh | H | H | H | H |
| 97 | p-FPh | Me | H | H | H |
| 98 | p-BrPh | H | H | H | H |
| 99 | p-BrPh | Me | H | H | H |

TABLE 1-continued

| Cpd No. | R¹ | R² | R³ | R⁴ | R⁵ |
|---|---|---|---|---|---|
| 100 | p-ClPh | H | H | H | H |
| 101 | p-ClPh | Me | H | H | H |
| 102 | p-ClPh | Et | H | H | H |
| 103 | m-ClPh | H | H | H | H |
| 104 | m-ClPh | Me | H | H | H |
| 105 | o-ClPh | H | H | H | H |
| 106 | o-ClPh | Me | H | H | H |
| 107 | 3,4-diClPh | H | H | H | H |
| 108 | p-MePh | H | H | H | H |
| 109 | p-MePh | Me | H | H | H |
| 110 | m-MePh | H | H | H | H |
| 111 | m-MePh | Me | H | H | H |
| 112 | o-MePh | H | H | H | H |
| 113 | o-MePh | Me | H | H | H |
| 114 | p-MeOPh | H | H | H | H |
| 115 | p-MeOPh | Me | H | H | H |
| 116 | m-MeOPh | H | H | H | H |
| 117 | m-MeOPh | Me | H | H | H |
| 118 | o-MeOPh | H | H | H | H |
| 119 | o-MeOPh | Me | H | H | H |
| 120 | p-NH2Ph | H | H | H | H |
| 121 | p-NH2Ph | Me | H | H | H |
| 122 | 3,4-diMeOPh | H | H | H | H |
| 123 | 3,4-diMeOPh | Me | H | H | H |
| 124 | 2-Np | H | H | H | H |
| 125 | 2-Np | Me | H | H | H |
| 126 | p-PhOPh | H | H | H | H |
| 127 | p-PhOPh | Me | H | H | H |
| 128 | p-BzOPh— | H | H | H | H |
| 129 | p-BzOPh— | Me | H | H | H |
| 130 | o-BzOPh— | H | H | H | H |
| 131 | o-BzOPh— | Me | H | H | H |
| 132 | p-HOPh | H | H | H | H |
| 133 | p-HOPh | Me | H | H | H |
| 134 | m-HOPh | H | H | H | H |
| 135 | m-HOPh | Me | H | H | H |
| 136 | p-CNPh | H | H | H | H |
| 137 | p-CNPh | Me | H | H | H |
| 138 | p-BozPh | H | H | H | H |
| 139 | p-BozPh | Me | H | H | H |
| 140 | 2-Thi | H | H | H | H |
| 141 | 2-Thi | Me | H | H | H |
| 142 | 2-Thi | Et | H | H | H |
| 143 | 3-Me-2-Thi | H | H | H | H |
| 144 | 5-Me-2-Thi | H | H | H | H |
| 145 | 5-Cl-2-Thi | H | H | H | H |
| 146 | 2-Fur | Me | H | H | H |
| 147 | 5-Me-2-Fur | Me | H | H | H |
| 148 | 1-Me-2-Pyrr | Me | H | H | H |
| 149 | 1,5-diMe-2-Pyrr | Me | H | H | H |
| 150 | 2-Pyr | H | H | H | H |
| 151 | 2-Pyr | Me | H | H | H |
| 152 | 3-Pyr | Me | H | H | H |
| 153 | 4-Pyr | Me | H | H | H |
| 154 | 6-Me-2-Pyr | H | H | H | H |
| 155 | 1-Me-2-Ind | Me | H | H | H |
| 156 | 5-MeO-2-Ind | Me | H | H | H |
| 157 | 5-Cl-2-Ind | Me | H | H | H |
| 158 | 4-Me-5-Oxa | Me | H | H | H |
| 159 | 4-Pyaz | Me | H | H | H |
| 160 | 5-Me-4-Pyaz | Me | H | H | H |
| 161 | p-HOOC-Ph | H | H | H | H |
| 162 | p-EtcPh | Me | H | H | H |
| 163 | p-CarPh | Me | H | H | H |
| 164 | H | p-HOOC—Ph | H | H | H |
| 165 | Me | p-MecPh | H | H | H |
| 166 | Me | p-CarPh | H | H | H |
| 167 | 3-Thi | H | H | H | H |
| 168 | 3-Thi | Me | H | H | H |
| 169 | Oc | Ph | H | H | H |
| 170 | Nn | Ph | H | H | H |
| 171 | Udc | Ph | H | H | H |
| 172 | Pdc | 2-Thi | H | H | H |
| 173 | Hdc | 2-Thi | H | H | H |
| 174 | iPn | Ph | H | H | H |
| 175 | 2-MePn | Ph | H | H | H |
| 176 | 1-MeHx | Ph | H | H | H |

TABLE 1-continued

| Cpd No. | R¹ | R² | R³ | R⁴ | R⁵ |
|---|---|---|---|---|---|
| 177 | iPn | 2-Thi | H | H | H |
| 178 | Hpdc | p-MePh | H | H | H |
| 179 | Nn | p-ClPh | H | H | H |
| 180 | Ph | ipn | H | H | H |
| 181 | Ph | Oc | H | H | H |
| 182 | Ph | Nn | H | H | H |
| 183 | Ph | Dc | H | H | H |
| 184 | Ph | Udc | H | H | H |
| 185 | Ph | Tdc | H | H | H |
| 186 | Ph | Pdc | H | H | H |
| 187 | Ph | Hpdc | H | H | H |
| 188 | Ph | Ndc | H | H | H |
| 189 | 2-Thi | ipr | H | H | H |
| 190 | H | Ph | EtcCH— | H | H |
| 191 | H | Ph | CNCH₂— | H | H |
| 192 | H | o-HOPh | H | H | H |
| 193 | Me | o-HOPh | H | H | H |
| 194 | H | o-BzOPh | H | H | H |
| 195 | Me | o-BzOPh | H | H | H |
| 196 | H | o-HOPh | Bz | H | H |
| 197 | Me | o-HOPh | Bz | H | H |
| 198 | Me | o-BzOPh | Bz | H | H |
| 199 | Me | p-HOPh | H | H | H |
| 200 | Me | p-BzOPh | H | H | H |
| 201 | H | m-HOPh | H | H | H |
| 202 | Me | m-HOPh | H | H | H |
| 203 | H | m-BzOPh | H | H | H |
| 204 | Me | m-BzOPh | H | H | H |
| 205 | Me | 2-Np | H | H | H |
| 206 | H | Ph | 2-EtcEt | H | H |

Of the compounds listed above, the following are preferred, that is to say Compounds No. 1, 4, 9, 15, 17, 18, 27, 41, 53, 57, 58, 60, 76, 93, 101, 108, 109, 114, 140, 141 and 146, and the more preferred compounds are:

1. 6-phenyl-1H-imidazo[1,2-b]pyrazole
15. 6-(p-chlorophenyl)-1H-imidazo[1,2-b]pyrazole
18. 7-methyl-6-phenyl-1H-imidazo[1,2-b]pyrazole
41. 7-phenyl-1H-imidazo[1,2-b]pyrazole
53. 6-(2-thienyl)-1H-imidazo[1,2-b]pyrazole
57. 7-methyl-6-(2-thienyl)-1H-imidazo[1,2-b]pyrazole
76. 6-methyl-7-phenyl-1H-imidazo[1,2-b]pyrazole
101. 6-methyl-7-(p-chlorophenyl)-1H-imidazo[1,2-b]pyrazole
108. 7-(p-methylphenyl)-1H-imidazo[1,2-b]pyrazole
140. 7-(2-thienyl)-1H-imidazo[1,2-b]pyrazole
141. 6-methyl-7-(2-thienyl)-1H-imidazo[1,2-b]pyrazole
and pharmaceutically acceptable salts thereof.

The compounds of the present invention can be prepared by a variety of processes of types which are well known in the art for the preparation of this kind of compound. In general terms, the compounds can be prepared by the ring closure of a compound of formula (II):

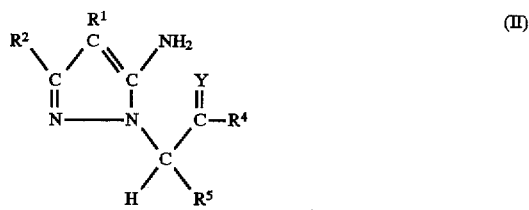
(II)

(in which R¹, R², R⁴ and R⁵ are as defined above, and the group represented by >C═Y is a carbonyl group or an acetal group) and then, if required, reacting the product with a compound of formula (III):

R³Z (III)

(in which: R³' represents any of the groups defined for R³ other than a hydrogen atom; and Z represents a 3 halogen atom, a C₁–C₄ alkanesulfonyloxy group or an arylsulfonyloxy group).

The compound of formula (II) may be prepared by reacting a pyrazole derivative of formula (IV):

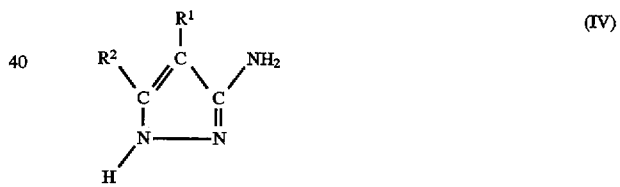
(IV)

(in which R¹ and R² are as defined above) with a compound of formula (V):

(V)

(in which: >C═Y, R⁴ and R⁵ are as defined above; and X represents a halogen atom, a C₁–C₄ alkanesulfonyloxy group or an arylsulfonyloxy group).

Examples of the substituents Z and X in the compounds of formulae (III) and (V), respectively, include: halogen atoms, such as the chlorine, bromine and iodine atoms; lower alkanesulfonyloxy groups, such as the methanesulfonyloxy and ethanesulfonyloxy groups; arylsulfonyloxy groups, such as the benzenesulfonyloxy and p-toluenesulfonyloxy groups. Examples of the acetal group which may be represented by >C═Y include di-(lower alkyl)acetal groups, such as the dimethylacetal and diethylacetal groups.

Reaction of the pyrazole derivative of formula (IV) with the carbonyl compound or acetal of formula (V) is normally and preferably effected in a solvent. There is no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride and chloroform; aromatic hydrocarbons, such as benzene, toluene and xylene; nitriles, such as acetonitrile; and amides, especially fatty acid amides, such as dimethylformamide.

The reaction is effected in the presence of a base, the nature of which is likewise not critical. Examples of suitable bases include: hydrides, especially alkali metal hydrides, such as sodium hydride; and organic bases, such as triethylamine.

The reaction can take place over a wide range of temperatures, and the precise reaction temperature is not critical to the invention. In general, we find it convenient to carry out the reaction at a temperature from 10° C. to around the boiling point of the solvent used. The time required for the reaction may also vary widely, depending on many factors, notably the reaction temperature and the nature of the reagents. However, provided that the reaction is effected under the preferred conditions outlined above, a period of from 1 to 10 hours will usually suffice.

Alternatively, the compound of formula (II) may be prepared by reacting a compound of formula (VI):

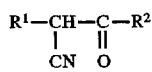  (VI)

(in which $R^1$ and $R^2$ are as defined above) with a compound of formula (VII):

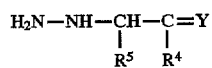  (VII)

(in which $R^4$, $R^5$ and Y are as defined above). The reaction is normally and preferably effected in a solvent, the nature of which is not critical, provided that it has no adverse effect upon the reaction. Examples of suitable solvents include: halogenated hydrocarbons, especially halogenated aliphatic hydrocarbons, such as chloroform, methylene chloride and carbon tetrachloride; aromatic hydrocarbons, such as benzene, toluene and xylene; alcohols, such as methanol, ethanol and isopropanol; amides, especially fatty acid amides, such as dimethylformamide; and nitriles, such as acetonitrile. The reaction will take place over a wide range of temperatures, and the precise reaction temperature chosen is not critical to the invention. In general, we find it convenient to carry out the reaction at a temperature in the range of from 10° C. to the boiling temperature of the solvent. The time required for the reaction may likewise vary widely, depending on many factors, notably the reaction temperature and the nature of the reagents. However, in most cases, a period of from 1 to 20 hours will normally suffice.

After completion of the reaction, the desired compound may be recovered from the reaction mixture by conventional means. For example, the reaction mixture may be poured into water, extracted with an organic solvent, and, if necessary, dried. It may then be freed from the solvent by distillation under reduced pressure. If required, it may then be further purified by conventional techniques, for example the various chromatography techniques, notably column chromatography.

The resulting compound of formula (II) may then be converted to a compound of formula (I) in which $R^3$ represents a hydrogen atom by a ring closure reaction. This may be effected by adding at least a catalytic amount of a suitable acid, e.g. an organic sulfonic acid (such as p-toluenesulfonic acid) or a mineral acid (such as hydrochloric acid or sulfuric acid), preferably hydrogen chloride in dioxane. The amount of acid catalyst may vary widely from a catalytic amount to a large excess, e.g. around 10 equivalents of acid per equivalent of compound of formula (II), in order to accelerate the reaction. The reaction is normally and preferably effected in an organic solvent, the nature of which is not critical, provided that it has no adverse effect upon the reaction. Examples of suitable solvents include: aromatic hydrocarbons, such as benzene, toluene and xylene; ethers, such as dioxane and tetrahydrofuran; and alcohols, such as methanol and ethanol. The reaction will take place over a wide range of temperatures, and the precise reaction temperature chosen is not critical to the invention. In general, we find it convenient to carry out the reaction at a temperature in the range of from room temperature to around the boiling point of the solvent used. The time required for the reaction may likewise vary widely, depending on many factors, notably the reaction temperature and the nature of the reagents. However, in most cases, a period of from 5 minutes to 2 hours will normally suffice.

After completion of the reaction, the desired compound of formula (Ia) may be recovered from the reaction mixture by conventional means. For example, one suitable recovery technique comprises: pouring the reaction mixture into ice-water; making it alkaline by the addition of ammonia or sodium bicarbonate; and then extracting the mixture with an organic solvent. The desired compound may then be obtained from the extract by standard techniques. If desired, the resulting compound may be further purified by such conventional techniques as recrystallization or the various chromatography techniques, notably column chromatography.

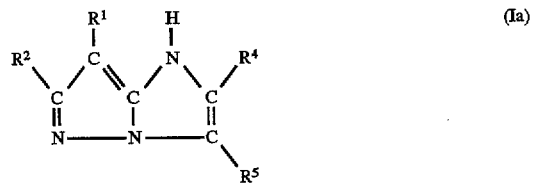  (Ia)

(in which $R^1$, $R^2$, $R^4$ and $R^5$ are as defined above).

The compound of formula (Ia) can also be obtained by heating the intermediate compound of formula (II) with PPA (polyphosphoric acid).

A compound of formula (I) in which $R^3$ represents a group other than a hydrogen atom, that is to say a compound of formula (Ib):

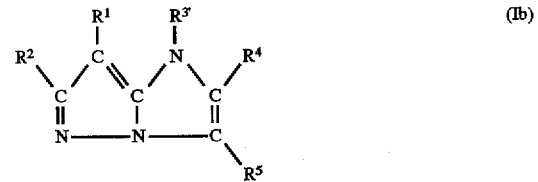  (Ib)

(in which $R^1$, $R^2$, $R^{3'}$, $R^4$ and $R^5$ are as defined above) may be prepared by reacting a compound of formula (Ia) with a compound of formula (III):

  (III)

(wherein Z and $R^{3'}$ are as defined above) in the presence of a base.

The reaction is normally and preferably effected in the presence of a solvent, the nature of which is not critical, provided that it has no adverse effect upon the reaction. Examples of suitable solvents include: halogenated hydrocarbons, especially halogenated aliphatic hydrocarbons, such as methylene chloride, chloroform and carbon tetrachloride; aromatic hydrocarbons, such as benzene, toluene and xylene; nitriles, such as acetonitrile; and amides, especially fatty acid amides, such as dimethylformamide and dimethylamide. The reaction will take place over a wide range of temperatures, and the precise reaction temperature chosen is not critical to the invention. In general, we find it convenient to carry out the reaction at a temperature in the range of from 0° C. to around the boiling point of the solvent used. The time required for the reaction may likewise vary widely, depending on many factors, notably the reaction temperature and the nature of the reagents. However, in most cases, a period of from 1 to 20 hours will normally suffice.

There is no particular restriction on the nature of the base, provided that it has no adverse effect on other parts of the molecule. Examples of suitable bases include: alkali metal hydroxides, such as sodium hydroxide and potassium hydroxide; alkali metal hydrides, such as sodium hydride; and organic bases, such as pyridine and triethylamine.

After completion of the reaction, desired compound may be recovered from the reaction mixture by conventional means, and the resulting compound may further be purified by such conventional techniques as recrystallization or the various chromatography techniques, notably column chromatography.

The compound of formula (IV) used as the starting material may be synthesized by the method of Takamizawa et al. [Yakugaku Zasshi 84, 1113 (1964)].

As is demonstrated by the biological activity data given hereafter, the imidazopyrazole derivatives of formula (I) and salts thereof exhibit excellent analgesic, anti-inflammatory and anti-allergic activities and they also exhibit an anti-ulcer effect. They also have a low toxicity and limited side effects. They are, therefore, expected to be of value in the treatment, alleviation and prophylaxis of a wide variety of disorders, for example for improving and treating chronic articular rheumatism, lumbago, neck-shoulder-arm syndrome, etc. They may also be used for the treatment and prophylaxis of allergic reactions. The compounds of the present invention are preferably administered as pharmaceutical compositions alone or in admixture with various pharmaceutically acceptable carriers, diluents or excipients, chosen having regard to the desired route of administration. The compounds may be administered orally or parenterally and suitable formulations include powders, granules, tablets, capsules, injections, suppositories, ointments and plasters. The dosage of the compounds of the invention will vary, depending upon the severity and nature of the disease or disorder, as well as the route, frequency and period of administration. However, a suitable dose for an adult human would be in the range of from 0.025 to 0.3 g, which may be administered in a single dose or in divided doses, e.g from one to three times per day for oral administration.

The preparation of the compounds of the present invention is further illustrated by the following non-limiting Examples 1 to 62. The use of these compounds to prepare pharmaceutical preparations is illustrated by the subsequent Examples 63 and 64. The biological activity of the compounds of the invention is then illustrated.

EXAMPLE 1

6-(4-Trifluoromethylphenyl)-1H-imidazo[1,2-b] pyrazole 1.0 g of 3-amino-5-(trifluoromethylphenyl)pyrazole and 5 ml of dimethylformamide were slowly added dropwise at room temperature, whilst stirring, to 0.15 g of a 55% w/w suspension of sodium hydride in mineral oil, which was itself suspended in 15 ml of dimethylformamide, and the resulting mixture was stirred for one hour at room temperature, after which 1.06 g of 2,2-dimethoxyethyl bromide was added at room temperature, whilst stirring. The mixture was then stirred at 70° to 80° C. for 3 hours. At the end of this time, the reaction mixture was partitioned between ethyl acetate and water. The ethyl acetate layer was washed with water and with an aqueous solution of sodium chloride, and was then dried over anhydrous magnesium sulfate. The solvent was then removed by evaporation under reduced pressure, to afford 700 mg of the intermediate compound, 3-amino-2-dimethoxyethyl-5-(4-trifluoromethylphenyl)pyrazole, as an oil.

A mixture of 700 mg of this intermediate compound and 7.0 g of polyphosphoric acid was stirred at 100° C. for 30 minutes, after which the reaction mixture was poured into ice-water and neutralized by the addition of sodium bicarbonate. The mixture was then extracted with ethyl acetate. The extract was dried over anhydrous magnesium sulfate, and the solvent was then removed by evaporation under reduced pressure, to afford the title compound as crude crystals. These crude crystal were purified by silica gel column chromatography using a 1:1 by volume mixture of ethyl acetate and hexane as the eluent, and the product was then recrystallized from a mixture of ethyl acetate and hexane to give 0.3 g of 6-(4-trifluoromethylphenyl)-1H-imidazo[1,2-b]pyrazole as pale brown needle-like crystals, melting at 134° to 135° C.

Elemental analysis: Calculated for $C_{12}H_8N_3F_3$: C, 57.37%; H, 3.21%; N, 16.73%; F, 22.69%. Found: C, 58.80%; H, 3.35%; N, 16.79%; F, 22.14%.

EXAMPLES 2 TO 5

The following compounds were synthesized in the same manner as described in Example 1.

TABLE 2

| Example No. | Compound No. | m.p. (°C.) |
|---|---|---|
| 2 | 4 | 134 to 135 |
| 3 | 1 | 187 to 189 |
| 4 | 18 | 198 to 200 |
| 5 | 9 | 201 to 204 |

EXAMPLE 6

6-(4-Fluorophenyl)-1H-imidazo[1,2-b]pyrazole 2.0 g of 3-amino-5-(4-fluorophenyl)pyrazole and 10 ml of dimethylformamide were slowly added dropwise at room temperature, whilst stirring, to 0.3 g of a 55% w/w suspension of sodium hydride in mineral oil, which was itself suspended in 20 ml of dimethylformamide, and the resulting mixture was then stirred for a further 1 hour at the same temperature. 2.1 g of 2,2-dimethoxyethyl bromide were then added dropwise at room temperature, whilst stirring. When the addition was complete, the mixture was stirred at 80° to 90° C. for 3 hours. At the end of this time, the reaction mixture was partitioned between ethyl acetate and water, and the ethyl acetate layer was washed with water and with an aqueous solution of sodium chloride. It was then dried over anhydrous magnesium sulfate, and the solvent was removed by evaporation under reduced pressure, to afford 1.2 g of the intermediate compound 3-amino-2-dimethoxyethyl-5-(4-fluorophenyl)pyrazole as an oil.

A mixture of 1.2 g of this intermediate compound, 10 ml of a 4N solution of hydrogen chloride in dioxane and 5 ml of ethanol was heated under reflux for 30 minutes, after which the solvent components of the mixture were removed by evaporation under reduced pressure. The residue was partitioned between ethyl acetate and an aqueous solution of sodium bicarbonate. The ethyl acetate layer was washed with an aqueous solution of sodium chloride and dried over anhydrous magnesium sulfate. The solvent was then removed by evaporation under reduced pressure, to afford the title compound as crude crystals. These crude crystals were purified by silica gel column chromatography using a 1:1 by volume mixture of ethyl acetate and hexane as the eluent, and the product was then recrystallized from a mixture of ethyl acetate and hexane to give 0.5 g of 6-(4-fluorophenyl)-1H-imidazo[1,2-b]pyrazole as pale violet needle-like crystals, melting at 225° to 227° C.

Elemental analysis: Calculated for $C_{11}H_8N_3F$: C, 65.67%; H, 4.01%; N, 20.88%; F, 9.44%. Found: C, 65.97%; H, 4.25%; N, 20.99%; F, 9.22%.

EXAMPLES 7 TO 19

The following compounds were synthesized in the same manner as described in Example 6.

TABLE 3

| Example No. | Compound No. | m.p. (°C.) |
|---|---|---|
| 7 | 6 | 197 to 200 |
| 8 | 15 | 203 to 205 |
| 9 | 42 | 235 to 237 |
| 10 | 19 | 190 to 193 |
| 11 | 20 | 206 to 208 |
| 12 | 22 | 179 to 180 |
| 13 | 25 | 160 to 163 |
| 14 | 29 | 147 to 149 |
| 15 | 23 | 206 to 208 |
| 16 | 24 | 163 to 165 |
| 17 | 17 | 169 to 172 |
| 18 | 48 | 242 to 245 |
| 19 | 12 | 225 to 227 |

EXAMPLE 20

6-(2-Thienyl)-1H-imidazo[1,2-b]pyrazole

A solution of 1.0 g of 5-(2-thienyl)-3-aminopyrazole in 5 ml of dimethylformamide was slowly added dropwise at room temperature, whilst stirring, to 0.26 g of a 55% w/w suspension of sodium hydride in mineral oil, which itself was suspended in 15 ml of dimethylformamide. The resulting mixture was then stirred for 1 hour at room temperature, after which 1.3 g of 2,2-dimethoxyethyl bromide was added, and the mixture was allowed to react at 50° to 60° C. for 3 hours. At the end of this time, the mixture was partitioned between ethyl acetate and water. The organic layer was washed with water and dried over anhydrous magnesium sulfate, and then the solvent was removed by evaporation under reduced pressure. The residue was purified by silica gel column chromatography using a 1:1 by volume mixture of ethyl acetate and hexane as the eluent, to afford 0.9 g of an intermediate compound as an oil.

A mixture of 0.9 g of this intermediate compound, 5 ml of a 4N solution of hydrogen chloride in dioxane and 3 ml of ethanol was heated under reflux for 10 minutes. The reaction mixture was then poured into ice-water and made basic by the addition of aqueous ammonia. The mixture was then extracted with ethyl acetate. The extract was washed with an aqueous solution of sodium chloride and dried over anhydrous magnesium sulfate. The solvent was then removed by evaporation under reduced pressure, and the residue was purified by silica gel column chromatography using a 1:1 by volume mixture of ethyl acetate and hexane as the eluent. The product was then recrystallized from a mixture of ethyl acetate and hexane, to afford 0.35 g of the title compound as colorless needle-like crystals melting at 199° to 203° C.

Elemental analysis: Calculated for $C_9H_7N_3S$ C, 57.12%; H, 3.73%; N, 22.21%; F, 16.94%. Found: C, 57.09%; H, 3.69%; N, 22.08%; F, 17.05%.

EXAMPLE 21

7-Methyl-6-(2-thienyl)-1H-imidazo[1,2-b]pyrazole

A solution of 1.9 g of 3-amino-4-methyl-5-(2-thienyl) pyrazole in 15 ml of dimethylformamide was slowly added dropwise at room temperature, whilst stirring, to 0.5 g of a 55% w/w suspension of sodium hydride in mineral oil, which itself was suspended in 10 ml of dimethylformamide. The resulting mixture was then stirred for 1 hour at room temperature, after which 2.0 g of 2,2-dimethoxyethyl bromide were added, and the mixture was allowed to react at 60° to 70° C. for 4 hours. At the end of this time, the resulting mixture was partitioned between ethyl acetate and water. The organic layer was washed with water and dried over anhydrous magnesium sulfate, after which the solvent was removed by evaporation under reduced pressure. The residue was purified by silica gel column chromatography using a 1:1 by volume mixture of ethyl acetate and hexane as the eluent, to afford 0.4 g of an intermediate compound as an oil.

A mixture of 0.4 g of this intermediate compound, 4 ml of a 4N solution of hydrogen chloride in dioxane and 1.5 ml of ethanol was heated under reflux for 10 minutes, after which the reaction mixture was poured into ice water and made basic by the addition of aqueous ammonia. The mixture was then extracted with ethyl acetate. The extract was washed with an aqueous solution of sodium chloride and dried over anhydrous magnesium sulfate. The solvent was then removed by evaporation under reduced pressure. The residue was purified by silica gel column chromatography using a 1:1 by volume mixture of ethyl acetate and hexane as the eluent, and the product was recrystallized from a mixture of ethyl acetate and hexane, to afford 0.14 g of the title compound as pale brown needle-like crystals, melting at 205° to 208° C.

Elemental analysis: Calculated for $C_{10}H_9N_3S$ C, 59.09%; H, 4.46%; N, 20.67%; S, 15.77%. Found: C, 59.12%; H, 4.49%; N, 20.52%; B, 16.06%.

EXAMPLE 22

6-(2-Furyl)-1H-imidazo[1,2-b]pyrazole

A solution of 2.0 g of 5-(2-furyl)-3-aminopyrazole in 5 ml of dimethylformamide was slowly added dropwise at room temperature, whilst stirring, to 0.59 g of a 55% w/w suspension of sodium hydride in mineral oil, which itself was suspended in 15 ml of dimethylformamide, and the resulting mixture was stirred for 1 hour at room temperature. 2.7 g of 2,2-dimethoxyethyl bromide were then added, and the mixture was allowed to react at 60° to 70° C. for 4 hours. At the end of this time, the resulting mixture was partitioned between ethyl acetate and water. The organic layer was washed with water and dried over anhydrous magnesium sulfate. The solvent was then removed by evaporation under reduced pressure. The residue was purified by silica gel column chromatography using a 1:1 by volume mixture of ethyl acetate and hexane as the eluent, to afford 1.2 g of an intermediate compound as an oil.

A mixture of 1.2 g of this intermediate compound, 10 ml of a 4N solution of hydrogen chloride in dioxane and 4 ml of ethanol was heated under reflux for 20 minutes, after which the reaction mixture was poured into ice water and made basic by the addition of aqueous ammonia. The mixture was then extracted with ethyl acetate. The extract was washed with an aqueous solution of sodium chloride and dried over anhydrous magnesium sulfate, after which the solvent was removed by evaporation under reduced pressure. The residue was purified by silica gel column chromatography using a 1:1 by volume mixture of ethyl acetate and hexane as the eluent, and the product was recrystallized from a mixture of ethyl acetate and hexane, to afford 0.44 g of the title compound as pale brown needle-like crystals, melting at 186° to 188° C.

Elemental analysis: Calculated for $C_9H_7N_3O$: C, 62.42%; C, 4.07%; N, 24.27%. Found: C, 62.36%; H, 4.23%; N, 24.14%.

EXAMPLES 23 TO 25

The following compounds were synthesized in the same manner as described in Examples 20 to 22.

TABLE 4

| Example No. | Compound No. | m.p. (°C.) |
|---|---|---|
| 23 | 59 | 230 to 235 |
| 24 | 58 | 167 to 169 |
| 25 | 65 | 205 to 208 |

EXAMPLE 26

1-Ethyl-6-(3-trifluoromethylphenyl)-1H-imidazo[1,2-b]-pyrazole Hydrochloride 800 mg of 6-(3-trifluoromethylphenyl)-1H-imidazo-[1,2-b]pyrazole and 5 ml of dimethylformamide were slowly added dropwise at room temperature, whilst stirring, to 76 mg of a 55% w/w suspension of sodium hydride in mineral oil, which was itself suspended in ml of dimethylformamide, and the resulting mixture was stirred for 30 minutes at room temperature. 497 mg of ethyl bromide were then added dropwise, whilst cooling with ice water, and the resulting mixture was stirred at room temperature for 30 minutes. The reaction mixture was then partitioned between ethyl acetate and water. The ethyl acetate layer was washed with water and with an aqueous solution of sodium chloride, in that order, and dried over anhydrous magnesium sulfate. The solvent was then removed by evaporation under reduced pressure. The product was then purified by silica gel column chromatography using a 1:1 by volume mixture of ethyl acetate and hexane as the eluent, to afford the title compound as an oil. The hydrochloride was formed from this oil by adding a 4N solution of hydrogen chloride in dioxane, and this was recrystallized from a mixture of acetone and diethyl ether, to afford 750 mg of 1-ethyl-6-(3-trifluoromethylphenyl)-1H-imidazo[1,2-b]pyrazole hydrochloride as pale brown prismatic crystals, melting at 135° to 141° C.

Elemental analysis: Calculated for $C_{14}H_{13}N_3ClF_3$: C, 53.26%; H, 4.15%; N, 13.31%; Cl, 11.23%; F, 18.05%. Found: C, 53.18%; H, 4.21%; N, 13.32%; Cl, 11.28%; F, 18.00%.

EXAMPLES 27 AND 28

The compounds shown in Table 5 were also prepared by the method described in Example 26.

TABLE 5

| Ex. No. | Compound No. | m.p. (°C.) |
|---|---|---|
| 27 | 197 (hydrochloride) | 185–187 |
| 28 | 198 | 125–127 |

EXAMPLE 29

7-Phenyl-1H-imidazo[1,2-b]pyrazole (Compound No. 41)

A solution of 2.0 g of 3-amino-4-phenylpyrazole in 10 ml of dimethylformamide was slowly added dropwise, whilst stirring at room temperature, to 0.55 g of a 55% by weight suspension of sodium hydride in mineral oil, which itself was suspended in 20 ml of dimethylformamide. The mixture was then stirred for 1 hour at room temperature, after which 1.8 ml of 2,2-dimethoxyethyl bromide was added, and then the whole mixture was stirred at 60°–70° C. for 4 hours. At the end of this time, the reaction mixture was partitioned between water and ethyl acetate. The organic phase was washed with water and dried over anhydrous magnesium sulfate. The solvent was then removed by evaporation under reduced pressure, to leave a residue, which was purified by column chromatography through silica gel, eluted with a 1:1 by volume mixture of ethyl acetate and hexane, to give 0.45 g of an intermediate compound as an oil.

A mixture of the whole of this oil, 5 ml of 4N hydrogen chloride in dioxane and 2 ml of ethanol was heated under reflux for 30 minutes. At the end of this time, the reaction mixture was poured into ice-water and made alkaline by the addition of aqueous ammonia. The mixture was then extracted with ethyl acetate. The extract was washed with an aqueous solution of sodium chloride and dried over anhydrous magnesium sulfate. The solvent was then distilled off under reduced pressure, and the residue was purified first by silica gel column chromatography using a 1:1 by volume mixture of ethyl acetate and hexane as the eluent, and then by recrystallization from a mixture of ethyl acetate and hexane, to give 0.2 g of the title compound in the form of colorless needles melting at 212°–214° C.

Elemental Analysis: Calculated for $C_{11}H_9N_3$: C, 72.11%; H, 4.95%; N, 22.94%. Found: C, 71.86%; H, 5.18%; N, 22.83%.

EXAMPLES 30 TO 53

Following substantially the same procedure as that described in Example 29, the following compounds were obtained.

TABLE 6

| Example No. | Compound No. | m.p. (°C.) |
|---|---|---|
| 30 | 76 | 164–166 |
| 31 | 80 | 164–166 |
| 32 | 140 | 181–182 |
| 33 | 100 | >230 |
| 34 | 101 | 220–224 |
| 35 | 108 | 210–212 |
| 36 | 109 | 231–233 |
| 37 | 93 | 190–191 |
| 38 | 97 | 185–187 |
| 39 | 114 | 204–205 |
| 40 | 115 | 178–180 |
| 41 | 170 | 144–145 |
| 42 | 90 | >260 |
| 43 | 92 | 205–207 |
| 44 | 104 | 214–216 |
| 45 | 106 | 180–182 |
| 46 | 117 | 186–187 |
| 47 | 119 | 194–195 |
| 48 | 123 | 193–196 |
| 49 | 124 | >250 |
| 50 | 125 | >250 |
| 51 | 141 | 178–180 |
| 52 | 167 | 192–194 |
| 53 | 168 | 176–178 |

EXAMPLE 54

2-Ethoxycarbonylmethyl-7-methyl-6-phenyl-1H-imidazo-[1,2-b]-pyrazole (Compound No. 38)

0.78 ml of ethyl 4-chloroacetoacetate was added to a solution of 1.0 g of 3-amino-4-methyl-5-phenyl-1H-pyrazole in 25 ml of acetonitrile, and then the mixture was stirred at room temperature for 4 days. At the end of this time, the crystals which separated were filtered off and the mother liquor was concentrated by evaporation under reduced pressure. The residue was partitioned between ethyl acetate and water, and the organic phase was washed with water and dried over anhydrous sodium sulfate. The solvent was distilled off under reduced pressure, and the residue was purified by column chromatography through silica gel, using a 1:1 by volume mixture of ethyl acetate and hexane as the eluent, to give 80 mg of the title compound in the form of an oil.

Nuclear Magnetic Resonance Spectrum (CDCl$_3$) δ ppm: 1.20 (3H, triplet, J=8.0 Hz); 2.15 (3H, singlet); 3.60 (2H, singlet) 4.15 (2H, quartet, J=8.0 Hz); 7.15 (1H, singlet); 7.2–7.8 (5H, multiplet).

EXAMPLE 55

1-Ethoxycarbonylmethyl-6-phenylimidazo[1,2-b]-pyrazole (Compound No. 190)

A solution of 0.4 g of 6-phenyl-1H-imidazo[1,2-b]-pyrazole in 10 ml of dimethylformamide was slowly added dropwise, whilst stirring at room temperature, to 96 mg of a 55% w/w suspension of sodium hydride in mineral oil, which was itself suspended in 10 ml of dimethylformamide, and then the mixture was stirred for a further 1 hour. At the end of this time, 0.24 ml of ethyl bromoacetate and 10 ml of dimethylformamide were added, and then the whole mixture was stirred at room temperature for 3 hours. The reaction mixture was then partitioned between ethyl acetate and water, and then the organic phase was washed with water and dried over anhydrous sodium sulfate. The solvent was distilled off under reduced pressure, and the residue was purified first by column chromatography through silica gel, eluted with a 1:1 by volume mixture of ethyl acetate and hexane, and then by recrystallization from a mixture of ethyl acetate and hexane, to give 0.38 g of the title compound in the form of plates melting at 85°–87° C.

Elemental Analysis: Calculated for $C_{15}H_{15}N_3O_2$: C, 66.90%; H, 5.61%; N, 15.60%; O, 11.89%. Found: C, 66.61%; H, 5.66%; N, 15.70%; O, 12.03%.

EXAMPLES 56 AND 57

Following substantially the same procedure as that described in Example 55, the following compounds were obtained.

TABLE 7

| Example No. | Compound No. | m.p. (°C.) |
|---|---|---|
| 56 | 206 | 70–75 |
| 57 | 191 | 117–119. |

EXAMPLE 58

7-4-Methylphenyl)-6-methyl-1H-imidazo[1,2-b]pyrazole (Compound No. 109)

A mixture of 1.7 g of 2-(4-methylphenyl)-3-oxobutyronitrile, 20 ml of ethanol and 1.5 g of 2,2-diethoxyethylhydrazine was heated under reflux for 7 hours. At the end of this time, 30 ml of 4N hydrogen chloride in dioxane were added, and then the whole mixture was heated under reflux for a further 30 minutes. After the mixture had been cooled, diethyl ether was added to precipitate crystals. These were collected by filtration and partitioned between ethyl acetate and dilute aqueous ammonia. The organic phase was separated, washed with water and dried over anhydrous magnesium sulfate. The solvent was then removed by distillation under reduced pressure, to leave a residue, which was recrystallized from a mixture of ethyl acetate and hexane, to give 1.5 g of the title compound. The physical and chemical properties of this compound were the same as those of the compound prepared as described in Example 36.

EXAMPLES 59 TO 61

The following compounds were also prepared by a procedure similar to that described in Example 58.

TABLE 8

| Ex. No. | Compound No. | m.p. (°C.) |
|---|---|---|
| 59 | 193 (hydrochloride) | 232–235 |
| 60 | 195 | 208–210 |
| 61 | 204 (hydrochloride) | 205–207 |

EXAMPLE 62

7-(4-Aminophenyl)-6-methyl-1H-imidazo[1,2-b]pyrazole Hydrochloride

A mixture of 2.5 g of 2-(4-t-butoxycarbonylaminophenyl)-3-oxobutyronitrile, 20 ml of ethanol and 1.4 g of 2,2-diethoxyethylhydrazine was heated under reflux for 2 hours. 20 ml of 4N hydrogen chloride in dioxane were added, and then the whole mixture was heated under reflux for a further 30 minutes. After the mixture had been cooled, ethyl acetate was added to precipitate crystals. These crystals were collected by filtration and recrystallized from ethanol to give 1.4 g of the title compound as pale brown plates melting at 180°–190° C.

EXAMPLE 63

Tablet

The following components were mixed:

| | |
|---|---|
| Compound of Example 35 | 50 mg |
| Corn starch | 40 mg |
| Lactose | 105 mg |
| HPC (produced by Nippon Soda) | 4 mg |
| Magnesium stearate | 1 mg |
| Total: | 200 mg |

The mixture was then formed by conventional means into tablets, each containing 200 mg of the above mixture.

EXAMPLE 64

Capsule

The following components were mixed:

| | |
|---|---|
| Compound of Example 4 | 100 mg |
| Corn starch | 70 mg |
| Lactose | 168.3 mg |
| Magnesium stearate | 1.7 mg |
| Total: | 340.0 mg |

The mixed powders were then passed through a 20 mesh (Tyler standard mesh) sieve, and packed into No. 2 gelatin capsules, 340 mg of powder per capsule.

BIOLOGICAL ACTIVITY

The following tests were conducted to determine the activity and toxicity of the compounds of the present invention. The drugs were all administered orally.

1. Anti-inflammatory effect (Carrageenan edema method)

The percent inhibition against carrageenan-induced edema in rats of the Wistar strain, using the conventional method of C. A. Winter, E. A. Risley, G. W. Nuss [J. Pharmacol., Exp. Therap., 141, 369 (1963)]. Except where otherwise noted, the dose of test compound was 50 mg/kg. The results are reported in Table 9.

2. Anti-inflammatory effect (Reversed passive alusas reaction)

The test animals were rats of the Sprague-Dawley strain, which had first been fasted for 17 hours. The hair was trimmed from their dorsal portions by means of a hair clipper, and 0.1 ml/site of anti-rat IgG rabbit serum was injected intracutaneously at the trimmed part to induce inflammation. Except in the case of the control animals, to which no anti-inflammatory drug was administered, the test drug was administered orally immediately before inflammation was induced. Except where otherwise noted, the dose of test compound was 50 mg/kg. Two hours after induction of inflammation, a 1% by volume solution of Evans blue in physiological saline was injected intravenously into the tail of each rat in an amount of 1 ml per each animal. 30 minutes after this injection, the rats were sacrificed with carbon dioxide and their skins were peeled off to extract the chromogen of the blue spots. In more detail, the skins were cut into small pieces and extracted with 5 ml of an extraction solvent at room temperature for 2 days. The supernatant obtained by centrifugation was then measured spectrophotometrically at an absorption wavelength of 605 nm. The percent inhibition of inflammation of the group of rats to which the test drug was administered was determined relative to the control group. The results are also reported in Table 9.

3. Analgesic effect

These tests were conducted according to the Randall-Selitto method using rats of the Wistar strain [L. O. Randall, J. J. Selitto; Arch. int. Pharmacodyn. 111, 409 (1957)]. Except where otherwise noted, the dose of test compound was 50 mg/kg. The results are also reported in Table 9.

4. Acute toxicity

The test animals employed were male mice of the ddy strain (age: 5 weeks). A suspension of the drug in a 0.5% by volume carboxymethyl cellulose solution was orally administered, and the animals were observed for 7 days. The dose of test compound was 300 mg/kg. The results are also reported in Table 9.

TABLE 9

| Cpd. of Ex. No. | Anti-inflammatory effect (Carrageenan) | Anti-inflammatory effect (Reversed passive alusas) | Analgesic effect (Randall-Selitto) | Toxicity (mouse) |
|---|---|---|---|---|
| 1 | 44.2% | — | 4/5 | 0/3 |
| 2 | 54.0% | 69.6% | 3/5 | 0/3 |
| 3 | 65.1% | 88.0% | 5/5 | 0/5 |
| 4 | 64.9% | 60.5% | 5/5 | 0/5 |
| 5 | 53.7% | 67.6% | 5/5 | 0/3 |
| 8 | 76.5% | 74.7% | 5/5 | 0/3 |
| 10 | 51.3% | 56.3% | 5/5 | 0/3 |
| 20 | 89.3% | 79.6% | 5/5 | 0/3 |
| 21 | 53.4% | 78.1%* | 5/5 | 0/3 |
| 22 | 76.3% | — | 4/5* | 0/3 |
| 24 | 71.9% | — | 4/5* | 0/3 |
| 29 | 63.2%* | 72.2%* | 5/5* | 0/3 |
| 30 | 50.0%* | — | 5/5* | 0/3 |
| 32 | 54.7%* | 82.5%* | 5/5* | 0/3 |
| 35 | 56.4%* | 69.9%* | 5/5* | 0.3 |

*The dose was 25 mg/kg.

The results of the above tests are also reported below, in terms of the $ID_{50}$ (anti-inflammatory tests) or $ED_{50}$ (analgesic test). The tests were also carried out using certain compounds of the prior art, and these results are reported in the following Table 10. The prior art compounds employed were Benzydamine (Merck Index, 10th Edition, Monograph No. 1128) and Mepirizole, whose systematic name is 3-methoxy-1-(4-methoxy-6-methylpyrimidin-2-yl)-5-methylpyrazole.

TABLE 10

| Cpd. of Ex. No. | Anti-inflammatory Carrageenan (mg/kg) | Anti-inflammatory reversed passive alusas (mg/kg) | Analgesic Randall-Selitto (mg/kg) |
|---|---|---|---|
| 3 | 36.6 | 13.9 | 6.1 |
| 4 | 34.1 | 26.7 | 2.4 |
| 20 | 17.1 | 7.0 | 8.0 |
| 21 | 22.3 | 7.9 | 10.0 |
| 29 | 20.1 | 14.8 | 5.1 |
| 30 | 25.0 | — | 5.9 |
| 32 | 23.4 | 10.9 | 6.9 |
| Benzydamine | 193 | — | >200 |
| Mepirizole | 106 | — | 63.9 |

5. 5-Lipoxydase inhibitory activity

The preparation of polymorphonuclear leukocytes was carried out by the method of Sbarra et al [Sbarra A. J. and Karnovsky, M. L.; J. Biol. Chem., 234, 1355–1362 (1959)]. Specifically, a 2% w/v aqueous casein solution was administered intraperitoneally to male guinea pigs of the Hartley strain, each weighing about 400–500 g. The polymorphonuclear leukocytes were harvested from the peritoneal exudate 14–16 hours after the administration. The preparation of enzyme was carried out by the method of Yoshimoto et al [Yoshimoto, T., Furukawa, M., Yamamoto, S., Horie, T. and Watanabe-Kohno, S.; Biochem. Biophys. Commun., 116, 612–618 (1983)]. The harvested polymorphonuclear leukocytes were suspended in a 50 mM phosphate buffer solution (pH=7.4) containing 10% ethylene glycol and 1 mM EDTA at a density of $1 \times 10^8$ cells/ml. The suspension was subjected to ultrasound twice, each time for 30 seconds at 20 KHz, and was then centrifuged for 10 minutes at 10,000 G. The supernatant was isolated as an enzyme fraction, which was stored at −80° C. The enzyme assay was carried out by a modification of Ochi's method [Ochi, K., Yoshimoto, T., Yamamoto., S., Taniguchi, K. and Miyamoto, T.; J. Biol. Chem., 258, 5754–5758 (1983)]. Specifically, 2 mM $CaCl_2$, 1 mM glutathione, 2 mM ATP (adenosine-5'-triphosphate), 16 μM [$^{14}C$]-arachidonic acid (0.16 μCi, dissolved in 5 μl ethanol), the test compound (dissolved in 4 μl DMSO) and the enzyme solution (containing 200 μg of protein) were made up to a final volume of 200 μl in a 50 mM potassium phosphate buffer solution (pH=7.4). The test compound and the enzyme were preincubated at 30° C. for 5 minutes. After the addition of the arachidonic acid, the mixture was incubated at 30° C. for 30 minutes. The reaction was stopped by the addition of 50 μl of 0.2N citric acid. The reaction mixture was then extracted with ethyl acetate and the extract was concentrated under a stream of nitrogen. The concentrate was subjected to thin layer chromatography and eluted with a 85:15:0.1 by volume mixture of diethyl ether, petroleum ether and acetic acid. The 5-hydroxyicosatetraenoic acid (5-HITE) fraction of the plate was identified with a radioactive scanner and the radioactivity was measured. The $IC_{50}$ (μg/ml) was calculated against the inhibitory rate of the production of 5-HITE of a control group, to which a test compound was not administered. The results are reported in Table 11.

TABLE 11

| Test compound Cpd. of Ex. No. | $IC_{50}$ |
|---|---|
| 10 | 1.1 |
| 11 | 2.0 |
| 12 | 0.94 |
| 41 | 0.66 |
| 30 | 0.50 |

The results of this test demonstrate that the compounds of the present invention have the ability to inhibit the activity of 5-lipoxygenase. A correlation between the inhibition of 5-lipoxygenase and anti-allergic activity is demonstrated by Yen, S. S. and Kreutner, W.; Agents and Actions, 10, 274–278 (1980), and Nijkamp, F. P. and Ramakers, A. G. M.; Europ. J. Pharmacol., 62, 121–122 (1980).

As can be seen from the results of the above tests, the compounds of the present invention have anti-inflammatory, analgesic and antipyretic activities, and are thus expected to be useful as therapeutic agents for improving and treating chronic articular rheumatism, lumbago, neck-shoulder-arm syndrome, etc.

6. Anti-ulcer activity

Suppression of gastric acid secretions was tested in rats by the Shay method [H. Shay; Gastroenterology, 5, 43 (1945)].

The results are reported in the following Table 12, which shows that the compounds of the present invention strongly suppressed gastric acid secretion, comparing well with a known anti-ulcer drug, cimetidine. Therefore, the compounds of the present invention are expected to have some anti-ulcer activity. This is all the more surprising since compounds having analgesic and anti-inflammatory activities are commonly known to cause ulcers, rather than to cure them.

TABLE 12

| Cpd of Ex. No. | Dosage (mg/kg - i.d.) | Suppression rate (%) |
|---|---|---|
| 3 | 10 | 66 |
| 3 | 30 | 85 |
| 4 | 10 | 67 |
| 4 | 30 | 100 |
| 20 | 10 | 84 |
| 20 | 30 | 93 |
| Cimetidine | 10 | 62 |
| Cimetidine | 30 | 58 |

As can be seen from the results of the above tests, the compounds of the present invention have anti-inflammatory, analgesic, antipyretic and anti-ulcer activities, and are thus expected to be useful as therapeutic agents for improving and treating chronic articular rheumatism, lumbago, neck-shoulder-arm syndrome, etc.

We claim:

1. A method for the treatment or prophylaxis of a disease or disorder selected from the group consisting of pain, inflammation and ulcers, by the administration to a mammal suffering from said disease or disorder of an effective amount of an active compound, wherein said active compound is selected from the group consisting of compounds of formula (I):

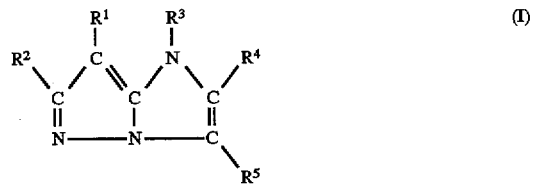

in which:

$R^1$ and $R^2$ are independently selected from the group consisting of: hydrogen atoms; $C_1$–$C_{25}$ alkyl groups; substituted $C_1$–$C_6$ alkyl groups having at least one substituent selected from the group consisting of substituents (a), defined below; $C_3$–$C_8$ cycloalkyl groups; $C_2$–$C_6$ alkenyl groups; aralkyl groups in which the alkyl part is $C_1$–$C_4$ and the aryl part is $C_6$–$C_{10}$ and is unsubstituted or has at least one substituent selected from the group consisting of substituents (b), defined below; arylalkenyl groups in which the aryl part is a $C_6$–$C_{10}$ aryl group which is unsubstituted or has at least one substituent selected from the group consisting of substituents (b), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b), defined below; aromatic heterocyclic groups which have from 5 to 8 ring atoms of which from 1 to 3 are hetero-atoms selected from the group consisting of nitrogen, oxygen and sulfur hetero-atoms, said group being unsubstituted or having at least one substituent selected from the group consisting of substituents (b), defined below, and being monocyclic or being fused to a benzene ring; cyano groups; and halogen atoms;

$R^3$ represents: a hydrogen atom; a $C_1$–$C_{25}$ alkyl group; a substituted $C_1$–$C_6$ alkyl group having at least one substituent selected from the group consisting of substituents (a), defined below; an aralkyl group in which the alkyl part is $C_1$–$C_4$ and the aryl part is $C_6$–$C_{10}$ and is unsubstituted or has at least one substituent selected from the group consisting of substituents (b), defined below; a $C_1$–$C_6$ aliphatic carboxylic acyl group; or an aromatic carboxylic acyl group in which the aryl part is a $C_6$–$C_{10}$ carbocyclic aryl group which is unsubstituted or has at least one substituent selected from the group consisting of substituents (b), defined below;

$R^4$ and $R^5$ are independently selected from the group consisting of: hydrogen atoms; $C_1$–$C_{25}$ alkyl groups; substituted $C_1$–$C_6$ alkyl groups having at least one substituent selected from the group consisting of substituents (a), defined below; $C_3$–$C_8$ cycloalkyl groups; $C_2$–$C_6$ alkenyl groups; aralkyl groups in which the alkyl part is $C_1$–$C_4$ and the aryl part is $C_6$–$C_{10}$ and is unsubstituted or has at least one substituent selected from the group consisting of substituents (b), defined below; arylalkenyl groups in which the aryl part is a $C_6$–$C_{10}$ aryl group which is unsubstituted or has at least one substituent selected from the group consisting of substituents (b), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b), defined below; and aromatic heterocyclic groups which have from 5 to 8 ring atoms of which from 1 to 3 are hetero-atoms selected from the group consisting of nitrogen, oxygen and sulfur hetero-atoms, said group being unsubstituted or having at least one substituent selected from the group consisting of substituents (b), defined below, and being monocyclic or being fused to a benzene ring;

substituents (a):

hydroxy groups, halogen atoms, carboxy groups, cyano groups, $C_2$–$C_7$ alkoxycarbonyl groups and aromatic heterocyclic groups which have from 5 to 8 ring atoms of which from 1 to 3 are hetero-atoms selected from the group consisting of nitrogen, oxygen and sulfur hetero-atoms, said group being unsubstituted or having at least one substituent selected from the group consisting of substituents (b), defined below, and being monocyclic or being fused to a benzene ring;

substituents (b):

$C_1$–$C_6$ alkyl groups; halogen atoms; $C_1$–$C_6$ alkoxy groups; aryloxy groups in which the aryl part is an unsubstituted $C_6$–$C_{10}$ carbocyclic aryl group; aralkyloxy groups in which the alkyl part is $C_1$–$C_4$ and the aryl part is $C_6$–$C_{10}$ and is unsubstituted; $C_1$–$C_6$ aliphatic carboxylic acyl groups; aromatic carboxylic acyl groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms; $C_1$–$C_6$ aliphatic carboxylic acyloxy groups; aromatic carboxylic acyloxy groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; aromatic carboxylic acylamino groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms; $C_1$–$C_4$ haloalkyl groups; carbamoyl groups; alkylcarbamoyl and dialkylcarbamoyl groups in which the or each alkyl group is $C_1$–$C_4$; carboxy groups; hydroxy groups; cyano groups; and $C_2$–$C_7$ alkoxycarbonyl groups;

and a pharmaceutically acceptable salt thereof;

with the proviso that when at least one of $R^1$ and $R^2$ represents the thienyl group, at least one of the other group of $R^1$, $R^2$, $R^3$, $R^4$, and substituents (a) represents an aromatic heterocyclic group other than thienyl.

2. The method of claim 1 in which:

$R^1$ and $R^2$ are independently selected from the group consisting of: hydrogen atoms; $C_1$–$C_{25}$ alkyl groups; substituted $C_1$–$C_6$ alkyl groups having at least one substituent selected from the group consisting of substituents (a), defined below; $C_3$–$C_8$ cycloalkyl groups; $C_2$–$C_6$ alkenyl groups; aralkyl groups in which the alkyl part is $C_1$–$C_4$ and the aryl part is $C_6$–$C_{10}$ and is unsubstituted or has at least one substituent selected from the group consisting of substituents (b), defined below; arylalkenyl groups in which the aryl part is a $C_6$–$C_{10}$ aryl group which is unsubstituted or has at least one substituent selected from the group consisting of substituents (b), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b), defined below; aromatic heterocyclic groups, defined below; cyano groups; and halogen atoms;

$R^3$ represents: a hydrogen atom; a $C_1$–$C_{25}$ alkyl group; a substituted $C_1$–$C_6$ alkyl group having at least one substituent selected from the group consisting of substituents (a), defined below; an aralkyl group in which the alkyl part is $C_1$–$C_4$ and the aryl part is $C_6$–$C_{10}$ and is unsubstituted or has at least one substituent selected from the group consisting of substituents (b), defined below; a $C_1$–$C_6$ aliphatic carboxylic acyl group; or an aromatic carboxylic acyl group in which the aryl part is a $C_6$–$C_{10}$ carbocyclic aryl group which is unsubstituted or has at least one substituent selected from the group consisting of substituents (b), defined below;

$R^4$ and $R^5$ are independently selected from the group consisting of: hydrogen atoms; $C_1$–$C_{25}$ alkyl groups; substituted $C_1$–$C_6$ alkyl groups having at least one substituent selected from the group consisting of substituents (a), defined below; $C_3$–$C_8$ cycloalkyl groups; $C_2$–$C_6$ alkenyl groups; aralkyl groups in which the alkyl part is $C_1$–$C_4$ and the aryl part is $C_6$–$C_{10}$ and is unsubstituted or has at least one substituent selected from the group consisting of substituents (b), defined below;

arylalkenyl groups in which the aryl part is a $C_6$–$C_{10}$ aryl group which is unsubstituted or has at least one substituent selected from the group consisting of substituents (b), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b), defined below; and aromatic heterocyclic groups, defined below;

substituents (a):

hydroxy groups, halogen atoms, carboxy groups, cyano groups, $C_2$–$C_7$ alkoxycarbonyl groups and aromatic heterocyclic groups; defined below;

substituents (b):

$C_1$–$C_6$ alkyl groups; halogen atoms; $C_1$–$C_6$ alkoxy groups; aryloxy groups in which the aryl part is an unsubstituted $C_6$–$C_{10}$ carbocyclic aryl group; aralkyloxy groups in which the alkyl part is $C_1$–$C_4$ and the aryl part is $C_6$–$C_{10}$ and is unsubstituted; $C_1$–$C_6$ aliphatic carboxylic acyl groups; aromatic carboxylic acyl groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms; $C_1$–$C_6$ aliphatic carboxylic acyloxy groups; aromatic carboxylic acyloxy groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; aromatic carboxylic acylamino groups in which the aryl part is a $C_6$–$C_{10}$ carbocyclic aryl group which is unsubstituted or has at least one substituent selected from the group consisting of $C_1$–$C_4$ alkyl groups, $C_1$–$C_4$ alkoxy groups and halogen atoms; $C_1$–$C_4$ haloalkyl groups; carbamoyl groups; alkylcarbamoyl and dialkylcarbamoyl groups in which the or each alkyl group is $C_1$–$C_4$; carboxy groups; hydroxy groups; cyano groups; and $C_2$–$C_7$ alkoxycarbonyl groups;

wherein when $R^1$, $R^2$, $R^4$, $R^5$ or substituent (a) represent an aromatic heterocyclic group which is substituted or unsubstituted, the aromatic heterocyclic group is selected from the group consisting of furyl, pyranyl, pyrrolyl, imidazolyl, pyrazolyl, thiazolyl, isothiazolyl, triazolyl, oxazolyl, isoxazolyl, pyridyl, pyrazinyl, pyrimidinyl, pyridazinyl, furazanyl, pyrrolidinyl, pyrrolinyl, imidazolidinyl, imidazolinyl, pyrazolidinyl, pyrazolinyl, piperidyl, piperazinyl, morpholinyl, thiomorpholinyl, azepinyl, azocinyl, triazocinyl, benzofuranyl, isobenzofuranyl, chromenyl, indolyl, isoindolyl, quinolyl, isoquinolyl, naphthyridinyl, quinoxalinyl, quinazolinyl, cinnolinyl, chromanyl, isochromanyl, indolinyl, isoindolinyl, 6-methyl-3-pyridyl, 2,6-dichloro-4-pyridyl, 2-methoxy-3-pyridyl, 6-methyl-2-pyridyl, 6-chloro-3-pyridyl, 6-(trifluoromethyl)-3-pyridyl, 5-chloro-2-pyridyl, 5-(trifluoromethyl)-2-furyl, 5-methyl-2-furyl, 2,5-dimethyl-3-furyl, 5-(trifluoromethyl)-2-thienyl, 3-methyl-2-thienyl, 5-methyl-2-thienyl, 5-chloro-2-thienyl, 1-methyl-2-pyrrolyl, 1,5-dimethyl-2-pyrrolyl, 3,5-dimethyl-2-pyrrolyl, 4-methyl-5-imidazolyl, 4-methyl-5-oxazolyl, 4-pyrazolyl, 5-methyl-4-pyrazolyl, 1-methyl-2-indolyl, 5-methoxy-2-indolyl, 5-chloro-2-indolyl, isoquinolyl, quinolyl;

and a pharmaceutically acceptable salt thereof.

3. The method of claim 2 wherein $R^1$ and $R^2$ are independently selected from the group consisting of: hydrogen atoms; $C_1$–$C_{11}$ alkyl groups; substituted $C_1$–$C_6$ alkyl groups having at least one substituent selected from the group consisting of substituents ($a^1$), defined below; $C_3$–$C_6$ cycloalkyl groups; $C_2$–$C_6$ alkenyl groups; aralkyl groups in which the alkyl part is $C_1$–$C_4$ and the aryl part is a phenyl group which is unsubstituted or has at least one substituent selected from the group consisting of substituents ($b^1$), defined below; phenylalkenyl groups in which the phenyl part is unsubstituted or has at least one substituent selected from the group consisting of substituents ($b^1$), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents ($b^1$), defined below; said aromatic heterocyclic groups; and halogen atoms;

substituents ($a^1$):

hydroxy groups, halogen atoms, carboxy groups, cyano groups, $C_2$–$C_4$ alkoxycarbonyl groups and said aromatic heterocyclic groups; said group being unsubstituted or having at least one substituent selected from the group consisting of substituents ($b^1$), defined below, and being monocyclic or being fused to a benzene ring;

substituents ($b^1$):

$C_1$–$C_4$ alkyl groups; halogen atoms; $C_1$–$C_4$ alkoxy groups; phenoxy groups; aralkyloxy groups in which the alkyl part is $C_1$–$C_4$ and the aryl part is an unsubstituted phenyl group; $C_2$–$C_6$ aliphatic carboxylic acyl groups; benzoyl groups which are unsubstituted or have at least one substituent selected from the group consisting of $C_1$–$C_4$ alkyl groups, $C_1$–$C_4$ alkoxy groups and halogen atoms; $C_1$–$C_6$ aliphatic carboxylic acyloxy groups; benzoyloxy groups which are unsubstituted or have at least one substituent selected from the group consisting of $C_1$–$C_4$ alkyl groups, $C_1$–$C_4$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; benzoylamino groups which are unsubstituted or have at least one substituent selected from the group consisting of $C_1$–$C_4$ alkyl groups, $C_1$–$C_4$ alkoxy groups and halogen atoms; $C_1$–$C_4$ haloalkyl groups; carbamoyl groups; alkylcarbamoyl and dialkylcarbamoyl groups in which the or each alkyl group is $C_1$–$C_4$; carboxy groups; and $C_2$–$C_6$ alkoxycarbonyl groups.

4. The method of claim 2, wherein $R^3$ represents: a hydrogen atom; a $C_1$–$C_{11}$ alkyl group; a substituted $C_1$–$C_6$ alkyl group having at least one substituent selected from the group consisting of substituents ($a^1$), defined below; an aralkyl group in which the alkyl part is $C_1$–$C_4$ and the aryl part is a phenyl group which is unsubstituted or has at least one substituent selected from the group consisting of substituents ($b^1$), defined below; a $C_1$–$C_6$ aliphatic carboxylic acyl group; or a benzoyl group which is unsubstituted or has at least one substituent selected from the group consisting of substituents ($b^1$), defined below;

substituents ($a^1$):

hydroxy groups, halogen atoms, carboxy groups, cyano groups, $C_2$–$C_4$ alkoxycarbonyl groups; and said aromatic heterocyclic groups;

substituents ($b^1$):

$C_1$–$C_4$ alkyl groups; halogen atoms; $C_1$–$C_4$ alkoxy groups; phenoxy groups; aralkyloxy groups in which the alkyl part is $C_1$–$C_4$ and the aryl part is an unsubstituted phenyl group; $C_2$–$C_6$ aliphatic carboxylic acyl groups; benzoyl groups which are unsubstituted or have at least one substituent selected from the group consisting of $C_1$–$C_4$ alkyl groups, $C_1$–$C_4$ alkoxy groups and halogen atoms; $C_1$–$C_6$ aliphatic carboxylic acyloxy groups; benzoyloxy groups which are unsubstituted or have at least one substituent selected from the group consisting of $C_1$–$C_4$ alkyl groups, $C_1$–$C_4$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; benzoylamino groups which are unsubstituted or have at least one substituent selected from the group consisting of $C_1$–$C_4$ alkyl groups, $C_1$–$C_4$ alkoxy groups and halogen atoms; $C_1$–$C_4$ haloalkyl groups; carbamoyl groups; alkylcarbamoyl and dialkylcarbamoyl groups in which the or each alkyl group is $C_1$–$C_4$; carboxy groups; and $C_2$–$C_5$ alkoxycarbonyl groups.

5. The method of claim 2, wherein $R^4$ and $R^5$ are independently selected from the group consisting of: hydrogen atoms; $C_1$–$C_{11}$ alkyl groups; substituted $C_1$–$C_6$ alkyl groups having at least one substituent selected from the group consisting of substituents ($a^1$), defined below; $C_3$–$C_6$ cycloalkyl groups; $C_2$–$C_6$ alkenyl groups; aralkyl groups in which the alkyl part is $C_1$–$C_4$ and the aryl part is a phenyl group which is unsubstituted or has at least one substituent selected from the group consisting of substituents ($b^1$), defined below; phenylalkenyl groups in which the phenyl part is unsubstituted or has at least one substituent selected from the group consisting of substituents ($b^1$), defined below, and the alkenyl part is $C_1$–$C_3$ alkenyl; $C_6$–$C_{10}$ aryl groups; $C_6$–$C_{10}$ aryl groups having at least one substituent selected from the group consisting of substituents ($b^1$), defined below; and said aromatic heterocyclic groups;

substituents (a¹):
a group selected from the group consisting of hydroxy groups, halogen atoms, carboxy groups, cyano groups, $C_2$–$C_4$ alkoxycarbonyl groups and said aromatic heterocyclic groups;

substituents (b¹):
a group selected from the group consisting of $C_1$–$C_4$ alkyl groups; halogen atoms; $C_1$–$C_4$ alkoxy groups; phenoxy groups; aralkyloxy groups in which the alkyl part is $C_1$–$C_4$ and the aryl part is an unsubstituted phenyl group; $C_2$–$C_6$ aliphatic carboxylic acyl groups; benzoyl groups which are unsubstituted or have at least one substituent selected from the group consisting of $C_1$–$C_4$ alkyl groups, $C_1$–$C_4$ alkoxy groups and halogen atoms; $C_1$–$C_6$ aliphatic carboxylic acyloxy groups; benzoyloxy groups which are unsubstituted or have at least one substituent selected from the group consisting of $C_1$–$C_4$ alkyl groups, $C_1$–$C_4$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; benzoylamino groups which are unsubstituted or have at least one substituent selected from the group consisting of $C_1$–$C_4$ alkyl groups, $C_1$–$C_4$ alkoxy groups and halogen atoms; $C_1$–$C_4$ haloalkyl groups; carbamoyl groups; alkylcarbamoyl and dialkylcarbamoyl groups in which the or each alkyl group is $C_1$–$C_4$; carboxy groups; and $C_2$–$C_6$ alkoxycarbonyl groups.

6. The method of claim 2, wherein:

$R^1$ and $R^2$ are independently selected from the group consisting of: hydrogen atoms; $C_1$–$C_{11}$ alkyl groups; substituted $C_1$–$C_6$ alkyl groups having at least one substituent selected from the group consisting of substituents (a¹), defined below; $C_3$–$C_6$ cycloalkyl groups; $C_2$–$C_6$ alkenyl groups; aralkyl groups in which the alkyl part is $C_1$–$C_4$ and the aryl part is a phenyl group which is unsubstituted or has at least one substituent selected from the group consisting of substituents (b¹), defined below; phenylalkenyl groups in which the phenyl part is unsubstituted or has at least one substituent selected from the group consisting of substituents (b¹), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b¹), defined below; said aromatic heterocyclic groups; and halogen atoms;

$R^3$ represents: a hydrogen atom; a $C_1$–$C_{11}$ alkyl group; a substituted $C_1$–$C_6$ alkyl group having at least one substituent selected from the group consisting of substituents (a¹), defined below; an aralkyl group in which the alkyl part is $C_1$–$C_4$ and the aryl part is a phenyl group which is unsubstituted or has at least one substituent selected from the group consisting of substituents (b¹), defined below; a $C_1$–$C_6$ aliphatic carboxylic acyl group; or a benzoyl group which is unsubstituted or has at least one substituent selected from the group consisting of substituents (b¹), defined below;

$R^4$ and $R^5$ are independently selected from the group consisting of: hydrogen atoms; $C_1$–$C_{11}$ alkyl groups; substituted $C_1$–$C_6$ alkyl groups having at least one substituent selected from the group consisting of substituents (a¹), defined below; $C_3$–$C_6$ cycloalkyl groups; $C_2$–$C_6$ alkenyl groups; aralkyl groups in which the alkyl part is $C_1$–$C_4$ and the aryl part is a phenyl group which is unsubstituted or has at least one substituent selected from the group consisting of substituents (b¹), defined below; phenylalkenyl groups in which the phenyl part is unsubstituted or has at least one substituent selected from the group consisting of substituents (b¹), defined below, and the alkenyl part is $C_2$–$C_3$ alkenyl; $C_6$–$C_{10}$ aryl groups; $C_6$–$C_{10}$ aryl groups having at least one substituent selected from the group consisting of substituents (b¹), defined below; and said aromatic heterocyclic groups;

substituents (a¹):
hydroxy groups, halogen atoms, carboxy groups, cyano groups, $C_2$–$C_4$ alkoxycarbonyl groups and said aromatic heterocyclic groups;

substituents (b¹):
$C_1$–$C_4$ alkyl groups; halogen atoms; $C_1$–$C_4$ alkoxy groups; phenoxy groups; aralkyloxy groups in which the alkyl part is $C_1$–$C_4$ and the aryl part is an unsubstituted phenyl group; $C_2$–$C_6$ aliphatic carboxylic acyl groups; benzoyl groups which are unsubstituted or have at least one substituent selected from the group consisting of $C_1$–$C_4$ alkyl groups, $C_1$–$C_4$ alkoxy groups and halogen atoms; $C_1$–$C_6$ aliphatic carboxylic acyloxy groups; benzoyloxy groups which are unsubstituted or have at least one substituent selected from the group consisting of $C_1$–$C_4$ alkyl groups, $C_1$–$C_4$ alkoxy groups and halogen atoms; amino groups; $C_1$–$C_4$ alkylamino groups; dialkylamino groups in which each alkyl part is $C_1$–$C_4$; $C_1$–$C_6$ aliphatic carboxylic acylamino groups; benzoylamino groups which are unsubstituted or have at least one substituent selected from the group consisting of $C_1$–$C_4$ alkyl groups, $C_1$–$C_4$ alkoxy groups and halogen atoms; $C_1$–$C_4$ haloalkyl groups; carbamoyl groups; alkylcarbamoyl and dialkylcarbamoyl groups in which the or each alkyl group is $C_1$–$C_4$; carboxy groups; and $C_2$–$C_5$ alkoxycarbonyl groups.

7. The method of claim 2, wherein:

$R^1$ and $R^2$ are independently selected from the group consisting of: hydrogen atoms; $C_1$–$C_6$ alkyl groups; substituted $C_1$–$C_4$ alkyl groups having at least one substituent selected from the group consisting of substituents (a²), defined below; benzyl groups in which the phenyl part is unsubstituted or has at least one substituent selected from the group consisting of substituents (b²), defined below; cinnamyl groups; phenyl groups; naphthyl groups; phenyl or naphthyl groups having at least one substituent selected from the group consisting of substituents (b²), defined below; said aromatic heterocyclic groups; and halogen atoms;

$R^3$ represents: a hydrogen atom; a $C_1$–$C_6$ alkyl group; a substituted $C_1$–$C_4$ alkyl group having at least one substituent selected from the group consisting of substituents (a²), defined below; a benzyl group which is unsubstituted or has at least one substituent selected from the group consisting of substituents (b²), defined below; a $C_2$–$C_4$ aliphatic carboxylic acyl group; or a benzoyl group which is unsubstituted or has at least one substituent selected from the group consisting of substituents (b²), defined below;

$R^4$ and $R^5$ are independently selected from the group consisting of: hydrogen atoms; $C_1$–$C_6$ alkyl groups; substituted $C_1$–$C_4$ alkyl groups having at least one substituent selected from the group consisting of substituents (a²), defined below; benzyl groups which are unsubstituted or have at least one substituent selected from the group consisting of substituents (b²), defined below; cinnamyl groups; phenyl groups; naphthyl groups; phenyl or naphthyl groups having at least one substituent selected from the group consisting of substituents (b²), defined below; and said aromatic heterocyclic groups;

substituents (a²):
a group selected from the group consisting of hydroxy groups, halogen atoms, cyano groups, carboxy groups, $C_2$–$C_4$ alkoxycarbonyl groups and said aromatic heterocyclic groups;

substituents (b²):
a group selected from the group consisting of $C_1$–$C_4$ alkyl groups; halogen atoms; $C_1$–$C_4$ alkoxy groups; trifluoromethyl groups; hydroxy groups; cyano groups; amino groups; carbamoyl groups; phenoxy groups; $C_2$–$C_6$ aliphatic carboxylic acyl groups; benzoyl groups which are unsubstituted or have at least one substituent selected from the group consisting of $C_1$–$C_2$ alkyl groups, $C_1$–$C_2$ alkoxy groups; halogen atoms; $C_2$–$C_4$ aliphatic carboxylic acyloxy groups; benzoyloxy groups which are unsubstituted or have at least one substituent selected from the group consisting of $C_1$–$C_2$ alkyl groups, $C_1$–$C_2$ alkoxy groups and halogen atoms; carboxy groups; and $C_2$–$C_5$ alkoxycarbonyl groups.

8. The method of claim 2, wherein:
$R^1$ represents a hydrogen atom or a $C_1$–$C_6$ alkyl group;
$R^2$ represents: a phenyl group; a substituted phenyl group having at least one substituent selected from the group consisting of substituents (b²), defined above; or said aromatic heterocyclic group;
$R^3$ represents: a hydrogen atom; a $C_1$–$C_4$ alkyl group; a substituted $C_1$–$C_4$ alkyl group having at least one substituent selected from the group consisting of substituents (a²), defined above; a $C_2$–$C_4$ aliphatic carboxylic acyl group; or a benzoyl group which is unsubstituted or has at least one substituent selected from the group consisting of substituents (b²), defined below;
$R^4$ and $R^5$ are independently selected from the group consisting of: hydrogen atoms; $C_1$–$C_6$ alkyl groups; substituted $C_1$–$C_4$ alkyl groups having at least one substituent selected from the group consisting of substituents (a²), defined above; and said aromatic heterocyclic groups.

9. The method of claim 2, wherein:
$R^1$ represents: a phenyl group; a substituted phenyl group having at least one substituent selected from the group consisting of substituents (b²), defined above; or said aromatic heterocyclic group;
$R^2$ represents a hydrogen atom or a $C_1$–$C_6$ alkyl group;
$R^3$ represents: a hydrogen atom; a $C_1$–$C_4$ alkyl group; a substituted $C_1$–$C_4$ alkyl group having at least one substituent selected from the group consisting of substituents (a²), defined above; a $C_2$–$C_4$ aliphatic carboxylic acyl group; or a benzoyl group which is unsubstituted or has at least one substituent selected from the group consisting of substituents (b²), defined below;
$R^4$ and $R^5$ are independently selected from the group consisting of: hydrogen atoms; $C_1$–$C_6$ alkyl groups; substituted $C_1$–$C_4$ alkyl groups having at least one substituent selected from the group consisting of substituents (a²), defined above; and said aromatic heterocyclic groups.

10. The method of claim 2, wherein:
$R^1$ represents a hydrogen atom or a methyl or ethyl group;
$R^2$ represents: a phenyl group; a substituted phenyl group having at least one substituent selected from the group consisting of methyl groups, chlorine atoms, trifluoromethyl groups and methoxy groups; a furyl group; or a furyl group having at least one substituent selected from the group consisting of methyl groups, methoxy groups, chlorine atoms and trifluoromethyl groups;
$R^3$ represents: a hydrogen atom; a $C_1$–$C_2$ alkyl group; a $C_2$–$C_4$ aliphatic carboxylic acyl group; a benzyl group; a cyanomethyl group; a ($C_1$–$C_4$ alkoxy) carbonylmethyl group; or a benzoyl group;
$R^4$ and $R^5$ are independently selected from the group consisting of: hydrogen atoms; $C_1$–$C_2$ alkyl groups; and substituted $C_1$–$C_2$ alkyl groups having at least one substituent selected from the group consisting of $C_2$–$C_3$ alkoxycarbonyl groups.

11. The method of claim 2, wherein:
$R^1$ represents: a phenyl group; a substituted phenyl group having at least one substituent selected from the group consisting of methyl groups, chlorine atoms, trifluoromethyl groups and methoxy groups; a furyl group; or a furyl group having at least one substituent selected from the group consisting of methyl groups, methoxy groups, chlorine atoms and trifluoromethyl groups;
$R^2$ represents a hydrogen atom or a methyl or ethyl group;
$R^3$ represents: a hydrogen atom; a $C_1$–$C_2$ alkyl group; a benzyl group; a cyanomethyl group; a ($C_1$–$C_4$ alkoxy) carbonylmethyl group; a $C_2$–$C_4$ aliphatic carboxylic acyl group; or a benzoyl group;
$R^4$ and $R^5$ are independently selected from the group consisting of: hydrogen atoms; $C_1$–$C_2$ alkyl groups; and substituted $C_1$–$C_2$ alkyl groups having at least one substituent selected from the group consisting of $C_2$–$C_3$ alkoxycarbonyl groups.

12. The method of claim 2, wherein said active compound is selected from the group consisting of:
6-phenyl-1H-imidazo[1,2-b]pyrazole;
6-(p-chlorophenyl)-1H-imidazo[1,2-b]pyrazole;
7-methyl-6-phenyl-1H-imidazo[1,2-b]pyrazole;
7-phenyl-1H-imidazo[1,2-b]pyrazole;
6-methyl-7-phenyl-1H-imidazo[1,2-b]pyrazole;
6-methyl-7-(p-chlorophenyl)-1H-imidazo[1,2-b]pyrazole;
7-(p-methylphenyl)-1H-imidazo[1,2-b]pyrazole;
and a pharmaceutically acceptable salt thereof.

* * * * *